United States Patent [19]

Haupt et al.

[11] Patent Number: 5,502,032
[45] Date of Patent: Mar. 26, 1996

[54] PEPTIDES, THE PREPARATION AND USE THEREOF

[75] Inventors: Andreas Haupt; Bernd Janssen, both of Ludwigshafen; Kurt Ritter; Dagmar Klinge, both of Heidelberg; Gerhard Keilhauer, Dannstadt-Schauernheim, all of Germany; Cynthia Romerdahl, Wayland, Mass.; Teresa Barlozzari, Brookline, Mass.; Xiao-dong Qian, Wellesley, Mass.

[73] Assignee: BASF Aktiengesellschaft, Ludwigshafen, Germany

[21] Appl. No.: 178,529

[22] Filed: Jan. 5, 1994

Related U.S. Application Data

[63] Continuation-in-part of Ser. No. 991,309, Dec. 16, 1992, abandoned.

[51] Int. Cl.$^6$ .......................... A61K 38/07; A61K 38/06
[52] U.S. Cl. ..................... 514/17; 514/18; 530/330; 530/331
[58] Field of Search ............. 514/18, 17; 530/331, 530/330

[56] References Cited

U.S. PATENT DOCUMENTS

| | | | |
|---|---|---|---|
| 4,946,830 | 8/1990 | Pulverer et al. | 514/23 |
| 4,978,744 | 12/1990 | Pettit et al. | 530/330 |
| 5,004,735 | 4/1991 | Okamoto et al. | 514/134 |
| 5,138,036 | 8/1992 | Pettit et al. | 530/325 |

OTHER PUBLICATIONS

Patel, Biochem. Soc. Trans., (1989) 17(5) p. 947.

Bundgaard, Biochem. Soc. Trans., (1989) 17(5) pp. 947–949.

*Primary Examiner*—Howard E. Schain
*Attorney, Agent, or Firm*—Keil & Weinkauf

[57] ABSTRACT

Novel peptides of the formula

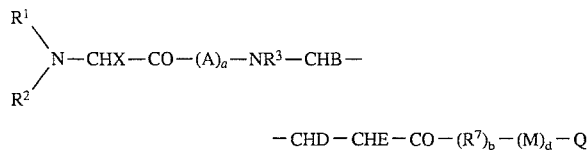

in which $R^1, R^2, X, A, R^3, B, D, E, R^7, M, Q, a, b$ and $d$ have the meanings stated in the description, and the preparation thereof are described. The novel substances have an antineoplastic effect.

13 Claims, No Drawings

PEPTIDES, THE PREPARATION AND USE THEREOF

This application is a continuation-in-part of application Ser. No. 07/991,309, filed on Dec. 16, 1992 now abandoned.

The invention described herein provides novel peptides and derivatives thereof which offer potentially improved therapeutic utilities for the treatment of neoplastic diseases as compared to Dolastatin-10. Furthermore, unlike dolastatin-10 which must be laboriously purified from scarce natural sources, the compounds of this invention may be conveniently synthesized as described in detail below. In addition, Dolastatin-10 is unstable to acid. It was described that even minor changes in the structure can cause complete loss of activity (Biochemical Pharmacology, vol. 40, no. 8, 1859–64, 1990).

Compounds of this invention include novel peptides of the formula I

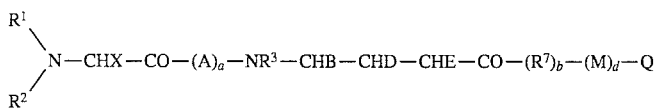

I where

- $R^1$ is alkoxy, preferably $C_{1-4}$; alkyl, preferably $C_{1-7}$; cycloalkyl, preferably $C_{3-6}$; alkylsulfonyl, preferably $C_{1-6}$; trifluoroethyl; fluoroethyl; difluoroethyl; trifluoroacetyl; amidino; ureyl; piperidinosulfonyl; morpholinosulfonyl; benzyloxycarbonyl; alkoxycarbonyl, preferably $C_{1-4}$; aminosulfonyl which may be substituted by alkyl, preferably $C_{1-5}$; hydroxy; phenylsulfonyl which may be substituted by up to three substituents independently selected from alkyl (preferably $C_{1-4}$), —N(CH$_3$)$_2$, nitro, halogen and CF$_3$; or NR$^8$R$^9$ where $R^8$ and $R^9$ may each be either hydrogen or alkyl, preferably $C_{1-4}$;

- $R^2$ is hydrogen; alkyl, preferably $C_{1-4}$; cycloalkyl, preferably $C_{3-7}$; acyl, preferably $C_{1-8}$; benzoyl or benzyl which may be substituted by up to three substituents independently selected from nitro, halogen, CF$_3$, alkyl (preferably $C_{1-4}$) and alkoxy (preferably $C_{1-4}$); or

- $R^1$—N—$R^2$ together may be a 5- or 6-membered heterocycle which may be unsubstituted or substituted with one or more substituents independently selected from phenyl, benzyl, alkyl (preferably $C_{1-4}$), N(CH$_3$)$_2$, nitro, oxo, thienyl, CONH$_2$, COOMe and COOEt;

- X is hydrogen, alkyl (preferably $C_{1-5}$), cycloalkyl (preferably cyclohexyl), —CH$_2$-cyclohexyl or benzyl;

- A is selected from the group consisting of valyl, isoleucyl, leucyl, allo-isoleucyl, α-aminoisobutanoyl, 3-tert-butylalanyl, 2-tert-butylglycyl, 3-cyclohexylalanyl, 2-ethylglycyl or 2-cyclohexylglycyl residues;

- $R^3$ is hydrogen or alkyl (preferably $C_{1-5}$);

- B is hydrogen, alkyl (preferably $C_{1-5}$), cycloalkyl (preferably cyclohexyl), —CH$_2$-cyclohexyl or benzyl;

- D is hydrogen, acetoxy, hydroxy, or alkoxy (preferably $C_{1-5}$);

- E is hydrogen, or alkyl (preferably $C_{1-5}$); or

- B and E together are —(CH$_2$)$_3$—, —(CH$_2$)$_2$—, —CH(CH$_3$)CH$_2$CH$_2$—, —CH(CH$_3$)CH$_2$—, —C(CH$_3$)$_2$CH$_2$CH$_2$—, or —C(CH$_3$)$_2$CH$_2$—;

- $R^7$ is —NR$^4$—CHG—CHK—CHL—CO—, or

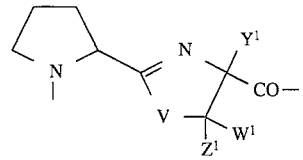

where V is oxygen or sulfur; $Y^1$ is hydrogen; $Z^1$ is hydrogen or lower alkyl (preferably $C_{1-4}$); or $Y^1$ and $Z^1$ may together form a bond; $W^1$ is hydrogen, alkyl (preferably $C_{1-6}$) or phenyl;

- $R^4$ is hydrogen or alkyl (preferably $C_{1-5}$);

- G is hydrogen, alkyl (preferably $C_{1-5}$), cyclohexyl, —CH$_2$-cyclohexyl, or benzyl;

- K is hydrogen, acetoxy, hydroxy, or alkoxy (preferably $C_{1-5}$);

- L is hydrogen, or alkyl (preferably $C_{1-5}$); or

- $R^4$ and G together are —(CH$_2$)$_4$—, —(CH$_2$)$_3$—, or —CH$_2$—CH(OH)—CH$_2$—;

- M is selected from the group consisting of 1-aminopentyl-1-carbonyl, valyl, 2-tert-butylglycyl, prolyl, hydroxyprolyl, isoleucyl, leucyl, 3-cyclohexylalanyl, phenylalanyl, tetrahydroisoquinolyl-2-carbonyl, 3-thiazolylalanyl, 3-thienylalanyl, histidyl, 2-aminoindyl-2-carbonyl, tyrosyl, 3-pyridylalanyl, 3-tert-butylalanyl, 2-cyclohexylglycyl, or 3-naphthylalanyl residues;

or $R^1R^2N$—CHX—CO— and A together are

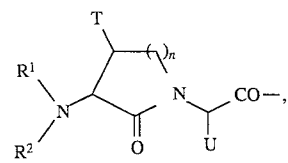

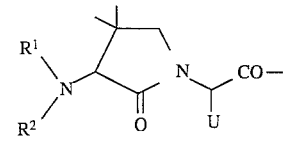

or

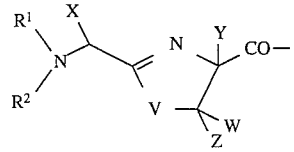

where

- T is hydrogen or lower alkyl (preferably methyl or ethyl); U is hydrogen or lower alkyl (preferably $C_{1-5}$); n is 1, 2, or 3; V is oxygen or sulfur; Y is hydrogen; Z is hydrogen or lower alkyl (preferably methyl); or Y and Z together may form a bond; W is hydrogen, lower alkyl (preferably $C_{1-4}$) or phenyl;

- a, b, and d are independently 0 or 1;

Q is hydroxy, alkoxy (preferably $C_{1-5}$), phenoxy, benzyloxy or a substituted or unsubstituted amino group;
provided that where b and d are 0, Q is not a hydroxy or alkoxy moiety;
and the salts thereof with physiologically tolerated acids.

This invention also provides methods for preparing the compounds of formula I, pharmaceutical compositions containing such compounds together with a pharmaceutically acceptable carrier and methods for using same for treating cancer in mammals.

One subclass of compounds of this invention includes compounds of formula I wherein $R^1$—N—$R^2$ is a 5- or 6-membered heterocycle of the formula

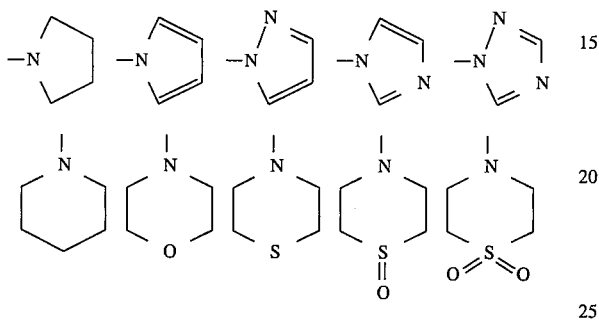

which may be unsubstituted or substituted with one or more substituents which may independently be selected from phenyl, benzyl, alkyl (preferably $C_{1-4}$), $N(CH_3)_2$, nitro, thienyl, $CONH_2$, COOEt or an oxo group.

Another subclass of compounds of this invention includes compounds of formula I wherein Q is an amino moiety of the formula $R^5$—N—$R^6$ wherein $R^5$ is H, or hydroxy, or $C_{1-7}$-alkoxy, or benzyloxy, or $C_{1-7}$-alkyl, or fluoroethyl, or difluoroethyl, or trifluoroethyl, or $C_{3-7}$-cycloalkyl, $R^6$ is H, or $C_{1-7}$-alkyl, or phenyl (which may be substituted by up to three substituents which may independently be $CF_3$, nitro, halogen, CONHBzl, $CON(Bzl)_2$, $C_{1-4}$-alkyl which may form a cyclic system, $C_{1-4}$-alkoxy, phenoxy, benzoxy, of $C_{1-7}$-alkyl-sulfonyl), or benzyl (which may be substituted by up to three substituents which may independently be $CF_3$, nitro, halogen, CONHBzl, $CON(Bzl)_2$, $C_{1-4}$-alkyl which may form a cyclic system, $C_{1-4}$-alkoxy, phenoxy, benzoxy, or $C_{1-7}$-alkylsulfonyl), or naphthyl (which may be substituted by up to two substituents which may independently be $CF_3$, nitro, halogen, CONHBzl, $CON(Bzl)_2$, $C_{1-4}$-alkyl, $C_{1-4}$-alkoxy, benzoxy, phenoxy, or $C_{1-7}$-alkyl-sulfonyl), or benzhydryl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or biphenyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or triphenylmethyl (which may be substituted by up to three substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzhydrylethyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzhydrylmethyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or naphthylmethyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or acenaphthyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or acenaphthylmethyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or pyridyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or picolyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzothiazolyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzisothiazolyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzopyrazolyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or benzoxazolyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or fluorenyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or aminofluorenyl (which may be substituted by up to two substituents which may independently be $CF_3$, nitro, halogen, CONHBzl, $CON(Bzl)_2$, $C_{1-4}$-alkyl, $C_{1-4}$-alkoxy, phenoxy, benzoxy, or $C_{1-7}$-alkyl-sulfonyl), or pyrimidyl (which may be substituted by up to two substituents which may independently be $CF_3$, nitro, halogen, COOEt, CONHBzl, $CON(Bzl)_2$, $C_{1-4}$-alkyl which may form a cyclic system, $C_{1-4}$-alkoxy, phenoxy, benzoxy, or $C_{1-7}$-alkyl-sulfonyl), or 5-membered hetaryl [which may be substituted by up to three substituents which may independently be $CF_3$, nitro, halogen, cyano, COOMe, COOEt, thiomethyl, thioethyl, thiophenyl, picolyl, acetyl, —$CH_2$—COOEt, $CONH_2$ CONHBzl, $CON(Bzl)_2$, $C_{1-4}$-alkyl which may form a cyclic system, $C_{1-4}$-alkoxy, phenoxy, benzoxy, phenyl (which may be substituted by up to four substituents which may independently be nitro, $CF_3$, halogen, or $C_{1-4}$-alkyl), benzyl (which may be substituted by up to four substituents which may independently be nitro, $CF_3$, halogen, $C_{1-4}$-alkyl, naphthyl, $C_{1-7}$-alkyl-sulfonyl, phenylsulfonyl, or $C_{1-4}$-dialkylamino)], or —$CHR^7$-5-membered hetaryl (which may be substituted by up to two substituents which may independently be $CF_3$, nitro, halogen, CONHBzl, $CON(Bzl)_2$, COOMe, COOEt, $COOCH(CH_3)_2$, $CONH_2$, COOBzl, $C_{1-4}$-alkyl, $C_{1-4}$-alkoxy, phenoxy, benzoxy, phenyl, benzyl, naphthyl, or $C_{1-7}$-alkyl-sulfonyl [$R^7$=H, linear or branched $C_{1-5}$-alkyl, benzyl; or $R^7$ and $R^5$ together form a group —$(CH_2)_3$— or —$(CH_2)_4$—]).

In another subclass of compounds of this invention $R^5$—N—$R^6$ together may form structures selected from the group consisting of

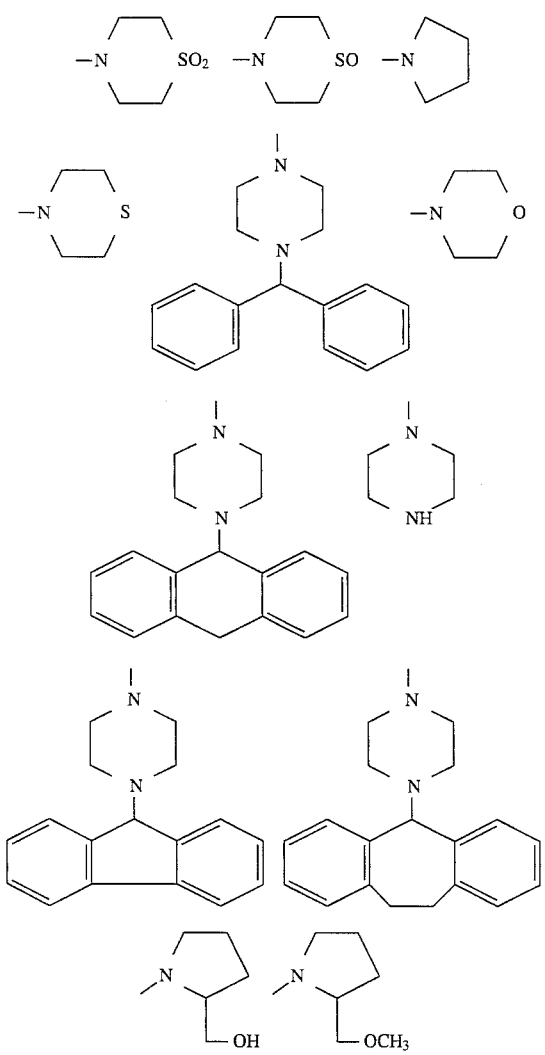

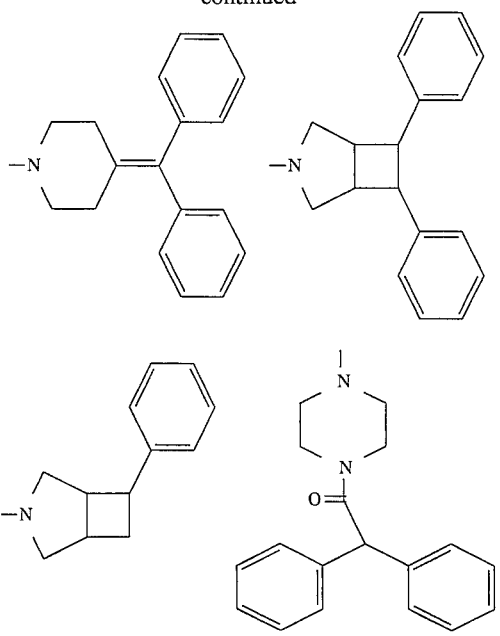

which may be unsubstituted or substituted with one or more substituents independently selected from the group consisting of $CF_3$, nitro, halogen, oxo, cyano, N,N-dimethylamino, CONHBzl, $CON(Bzl)_2$, $C_{1-6}$-alkyl (which may form a cyclic system), $C_{1-4}$-alkoxy, phenoxy, benzoxy, naphthyl, pyrimidyl, COOEt, COOBzl, $C_{3-6}$-cycloalkyl, pyrrolidinyl, piperidinyl, thienyl, pyrrolyl, —$CH_2$—CO—$NCH(CH_3)_2$, —$CH_2$—CO—$N(CH_2)_4$, —$CH_2$—CO—$N(CH_2)_4O$, benzyl (which may be substituted by up to three substituents independently selected from the group consisting of nitro, halogen, $CF_3$, thiomethyl or the corresponding sulfoxide or sulfone, thioethyl or the corresponding sulfoxide or sulfone, $C_{1-4}$-alkyl, and $C_{1-4}$-alkoxy), and phenyl (which may be substituted by up to three substituents independently selected from the group consisting of nitro, halogen, $CF_3$, thiomethyl, thioethyl, $C_{1-4}$-alkyl, and $C_{1-4}$-alkoxy).

Another subclass of compounds of this invention includes compounds of formula I wherein b is zero.

Yet another subclass of compounds of this invention includes compounds of formula I wherein d is zero, b is —$NR^4$—CHG—CHK—CHL—CO—, and Q is not a hydroxy or alkoxy group.

Still another subclass of compounds of this invention includes compounds of formula I wherein b and d are zero, and Q is not a hydroxy or alkoxy group.

Another subclass of compounds of this invention includes compounds of formula I wherein d is 0 and $R^7$ is

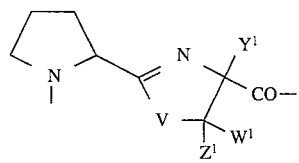

Another subclass of compounds of this invention includes compounds of formula I wherein a is 0.

Yet another subclass of compounds of this invention includes compounds of formula I wherein a and d are 0.

Another subclass of compounds of this invention includes compounds of formula I wherein b and d are 1 and Q is a hydroxy, $C_{1-4}$-alkoxy or benzyloxy moiety.

Preferred are compounds where the substituents have the following meanings:

$R^1$ is ethyl, methyl, trifluoroethyl, fluoroethyl, difluoroethyl, isopropyl, n-propyl, n-butyl, n-pentyl, cyclopropyl, cyclopentyl, ureyl, mesyl, tosyl, naphtylsulfonyl, phenylsulfonyl, 2,4,6-trimethylsulfonyl, benzyloxycarbonyl, tert.butoxycarbonyl, methoxycarbonyl, morpholinosulfonyl, tert.butylaminosulfonyl, methylaminosulfonyl, trifluoroacetyl, $NH_2$, $N(CH_3)_2$, $N(CH_2CH_3)_2$, $N[CH(CH_3)_2]_2$, amidino or $CH_3O$—, $R^2$ is H, methyl, ethyl, isopropyl, n-propyl, n-butyl, cyclopropyl, formyl, acetyl, propionyl, $(CH_3)_2CHCO$—, pivaloyl, benzoyl or

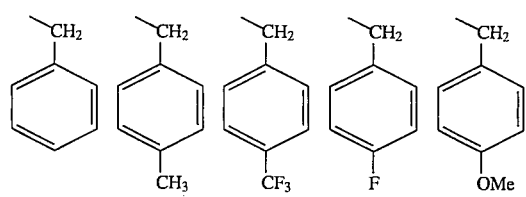

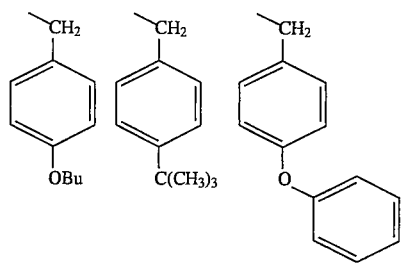

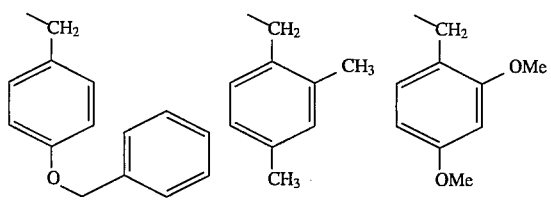

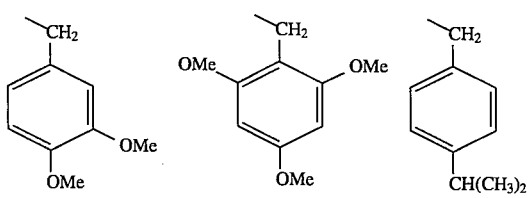

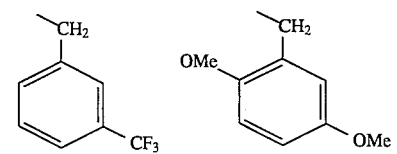

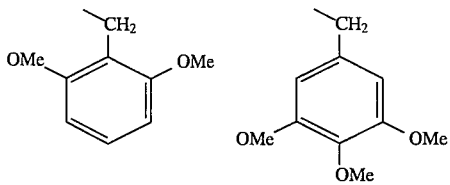

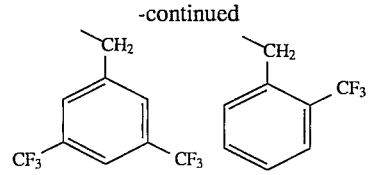

or $R^1$—N—$R^2$ together are

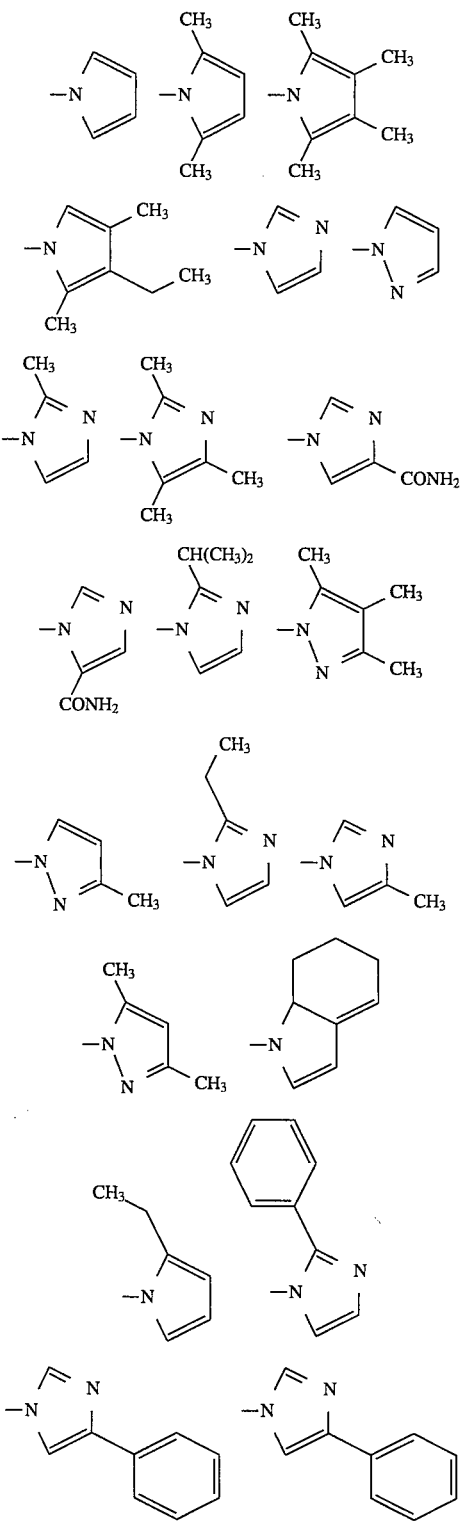

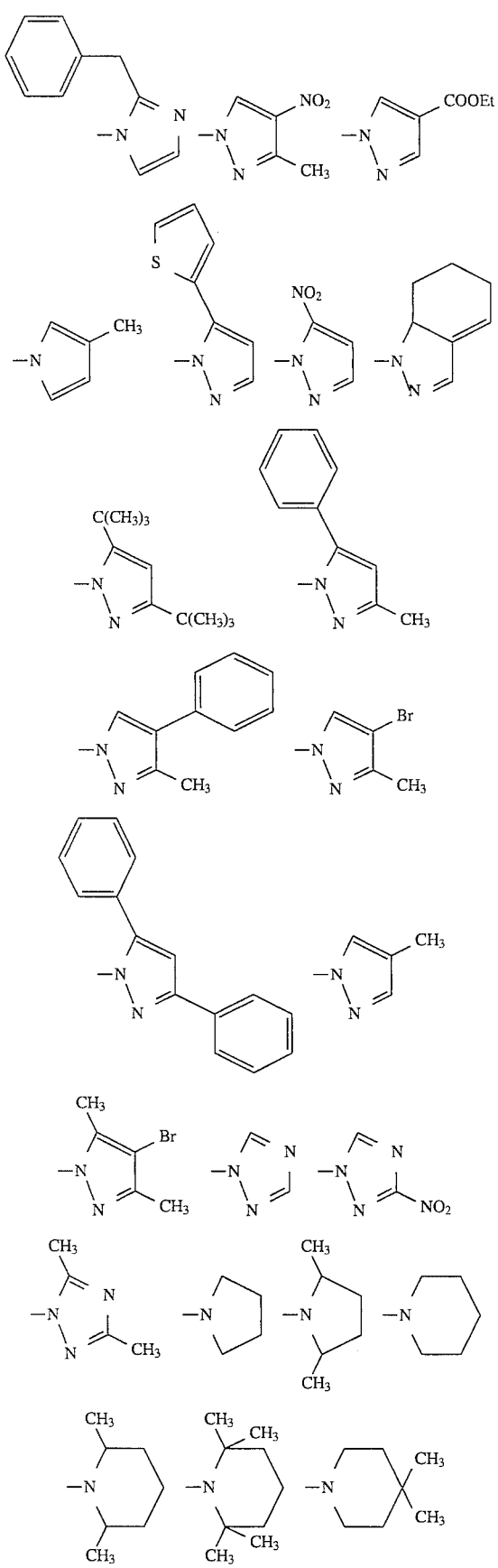

X is hydrogen, methyl, ethyl, isopropyl, —CH$_2$CH(CH$_3$)$_2$, —CH(CH$_3$)CH$_2$CH$_3$, tert.butyl, —CH$_2$-cyclohexyl, or benzyl;

A is valyl, isoleucyl, leucyl, allo-isoleucyl, 3-tert-butylalanyl, 2-tert-butylglycyl, 3-cyclohexylalanyl, 2-ethylglycyl, or 2-cyclohexylglycyl;

R$^3$ is hydrogen, methyl, or ethyl;

B is hydrogen, methyl, ethyl, isopropyl, —CH$_2$CH(CH$_3$)$_2$, —CH(CH$_3$)CH$_2$CH$_3$, tert.butyl, —CH$_2$-cyclohexyl, or benzyl;

D is hydrogen, hydroxy, methoxy, ethoxy, isopropyloxy or tert-butyloxy;

E is hydrogen, methyl, ethyl, isopropyl or tert-butyl; or

B and E together may form a group —(CH$_2$)$_2$—, —(CH$_2$)$_3$—, —CH(CH$_3$)—CH$_2$—, or —C(CH$_3$)$_2$—CH$_2$—;

R$^7$ is —NR$^4$—CHG—CHK—CHL—CO—, or

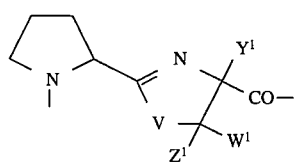

where
V is oxygen or sulfur; $Y^1$ is hydrogen; $Z^1$ is hydrogen or methyl; or $Y^1$ and $Z^1$ may together form a bond; $W^1$ is hydrogen, methyl, ethyl, isopropyl, tert-butyl or phenyl;

$R^4$ is hydrogen or methyl;

G is hydrogen, methyl, ethyl, isopropyl, $-CH_2CH(CH_3)_2$, $-CH(CH_3)CH_2CH_3$, tert.butyl, $-CH_2$-cyclohexyl, or benzyl;

K is hydrogen, hydroxy, methoxy, ethoxy, isopropyloxy or tert-butyloxy;

L is hydrogen, methyl, ethyl or isopropyl; or $R^4$ and G together are $-(CH_2)_4-$, $-(CH_2)_3-$, or $-CH_2-CH(OH)-CH_2-$ M is selected from the group consisting of valyl, 2-tert-butylglycyl, prolyl, hydroxyprolyl, isoleucyl, leucyl, 3-cyclohexylalanyl, phenylalanyl, tetrahydroisoquinolyl-2-carbonyl, 3-thiazolylalanyl, 3-thienylalanyl, 2-aminoindyl-2-carbonyl, tyrosyl, 3-pyridylalanyl, 3-tert-butylalanyl, 2-cyclohexylglycyl, or 3-naphthylalanyl residues;

a,b and d are independently 0 or 1;

or $R^1R^2N-CHX-CO$ and A together are

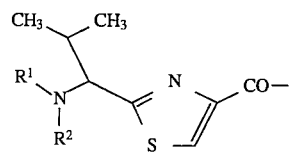

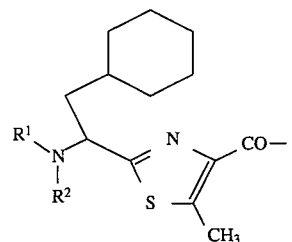

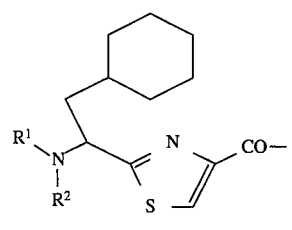

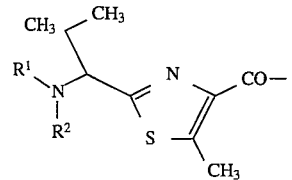

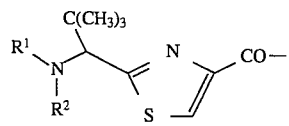

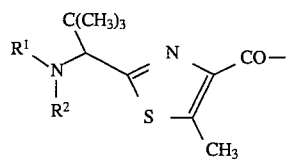

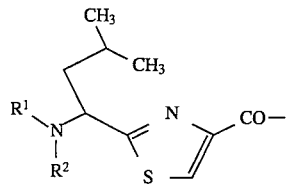

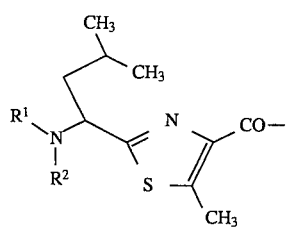

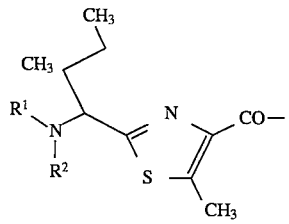

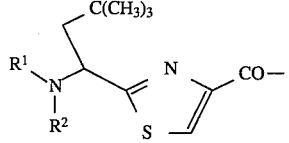

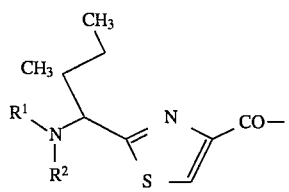

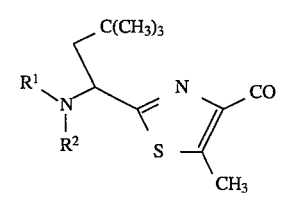

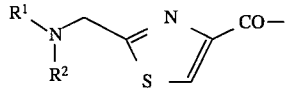

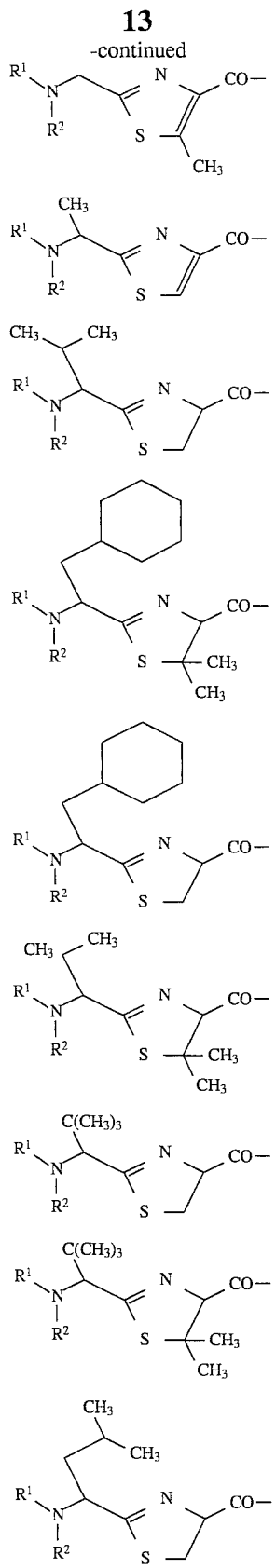
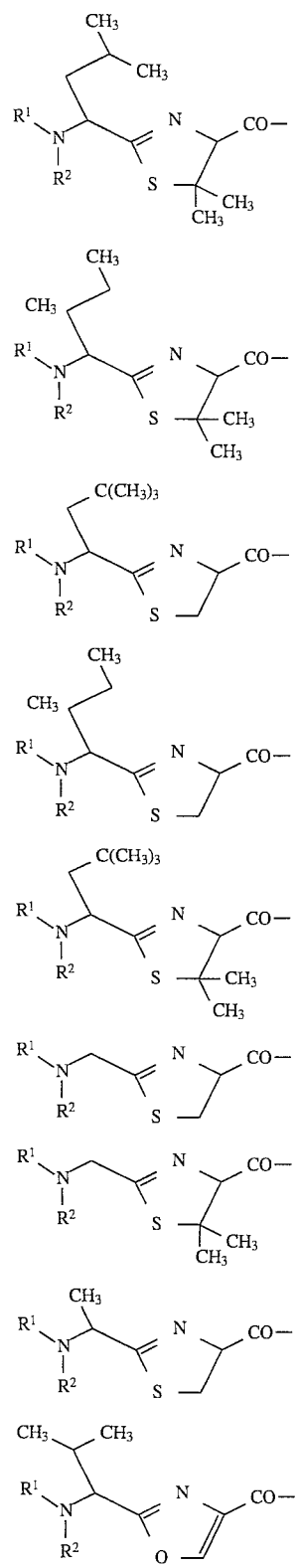

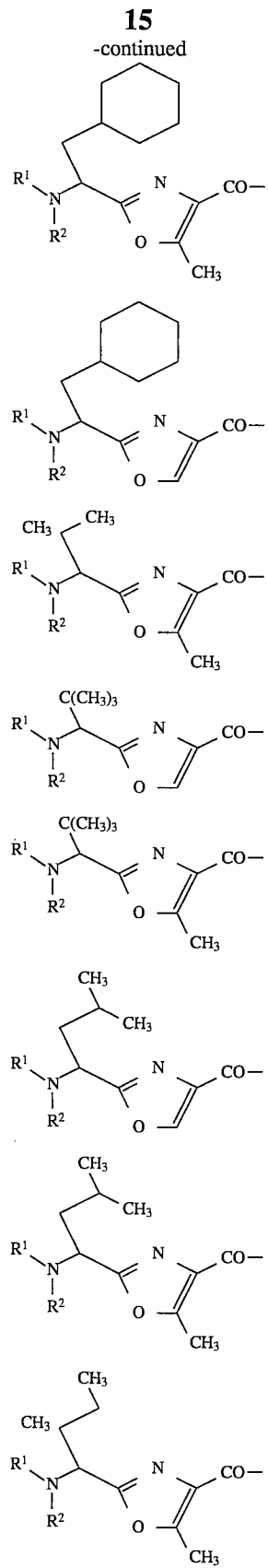
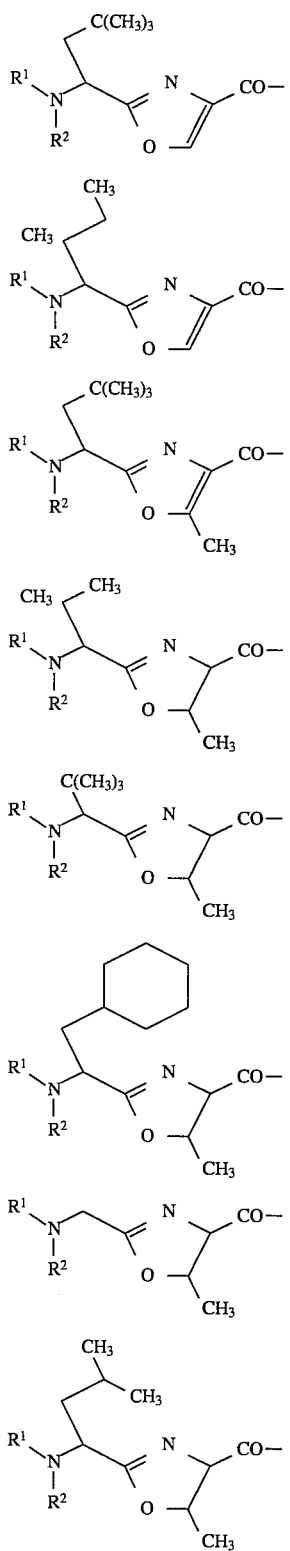

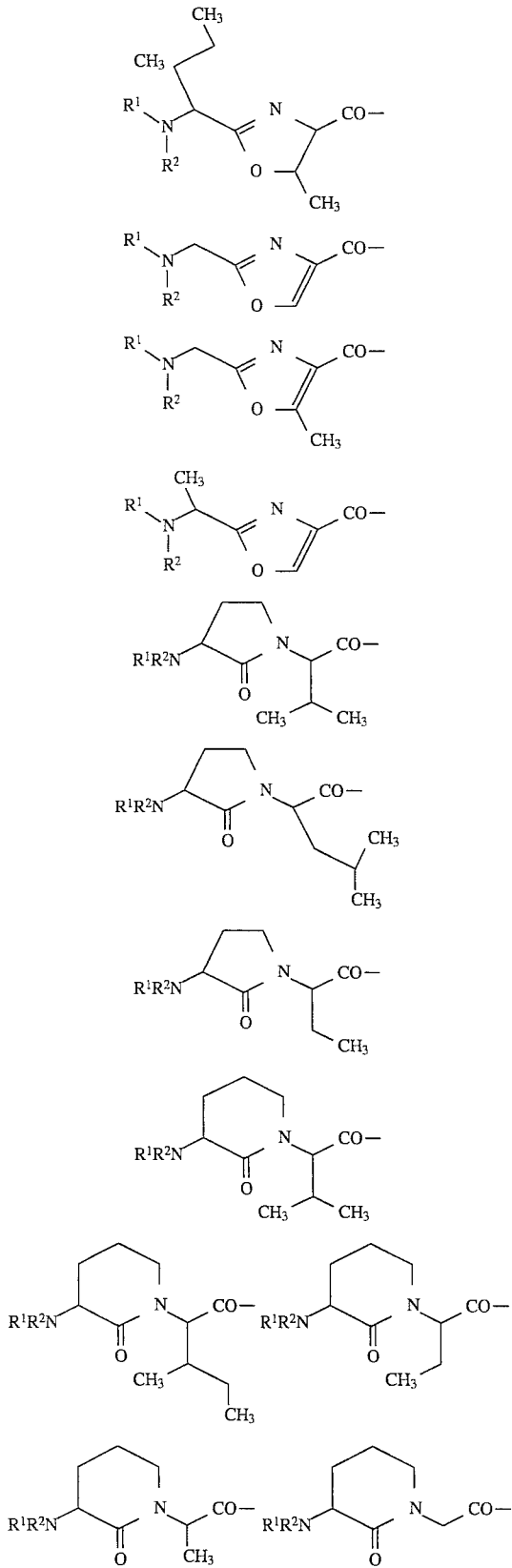
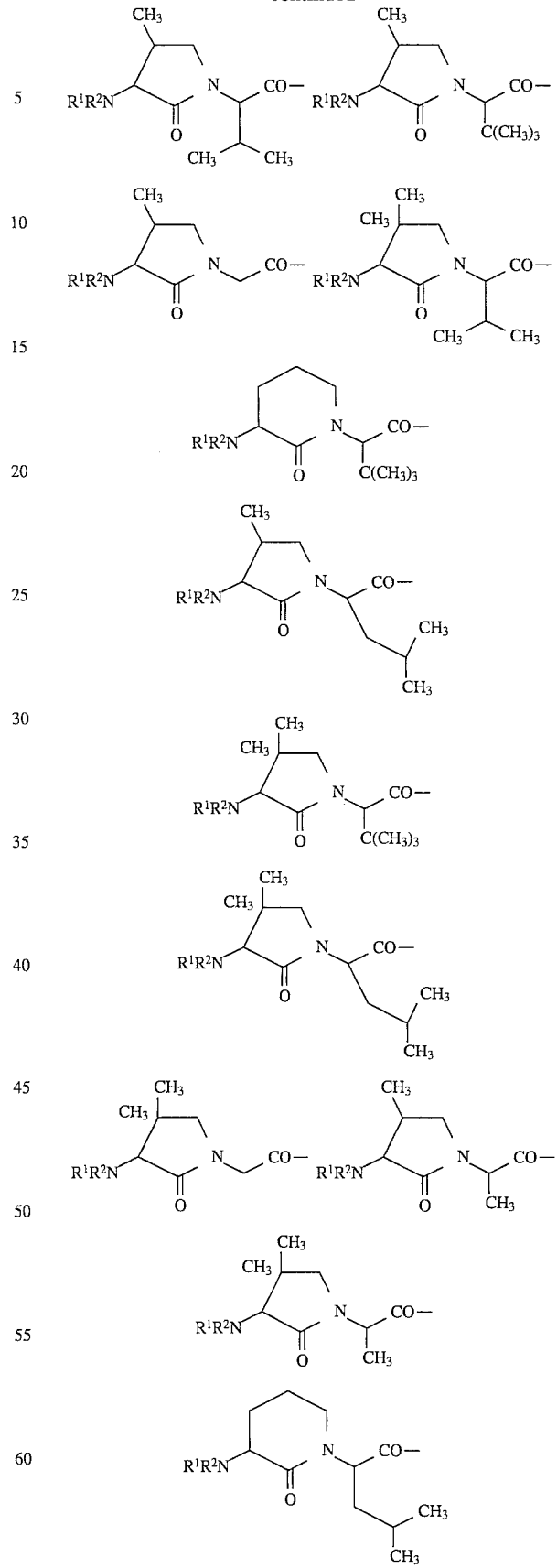

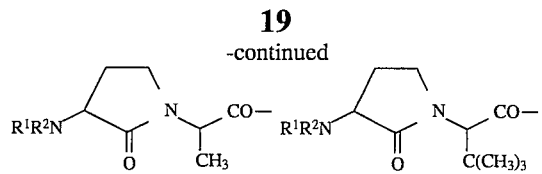
Q is a hydroxyl, $C_{1-5}$-alkoxyl, benzyloxyl or a amino moiety —$NR^5R^6$ where
$R^5$ is hydrogen, methyl, ethyl, trifluoroethyl, fluoroethyl, difluoroethyl, propyl, isopropyl, or
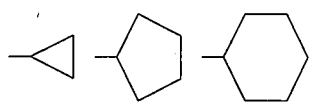
$R^6$ is hydrogen, methyl, ethyl, trifluoroethyl, propyl, isopropyl, tert-butyl, or
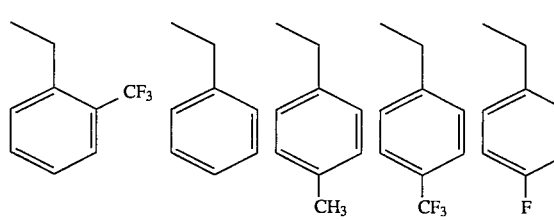
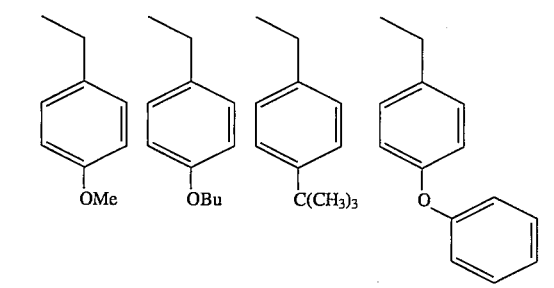
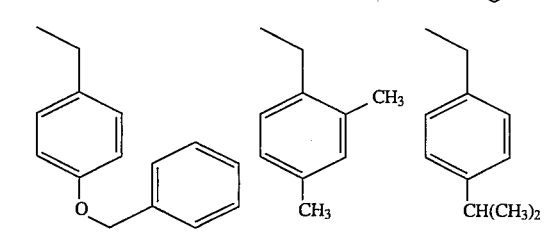
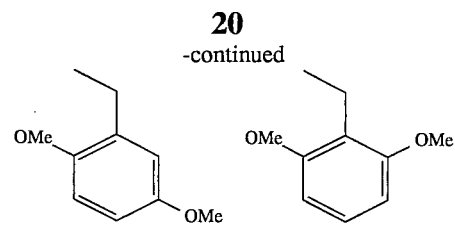
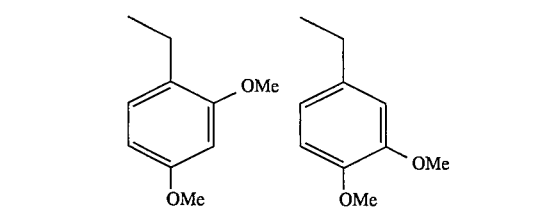
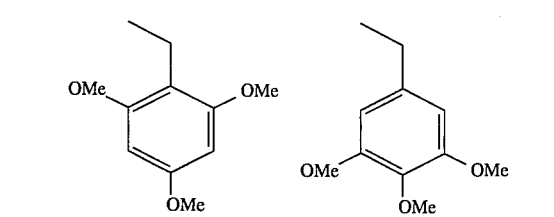

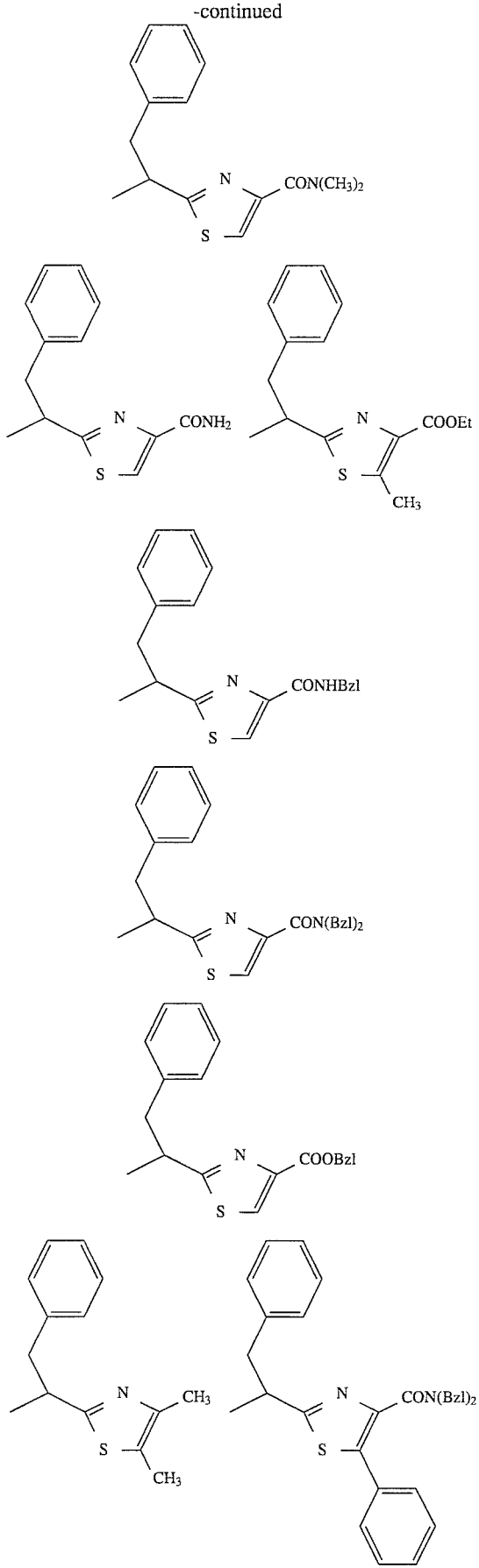
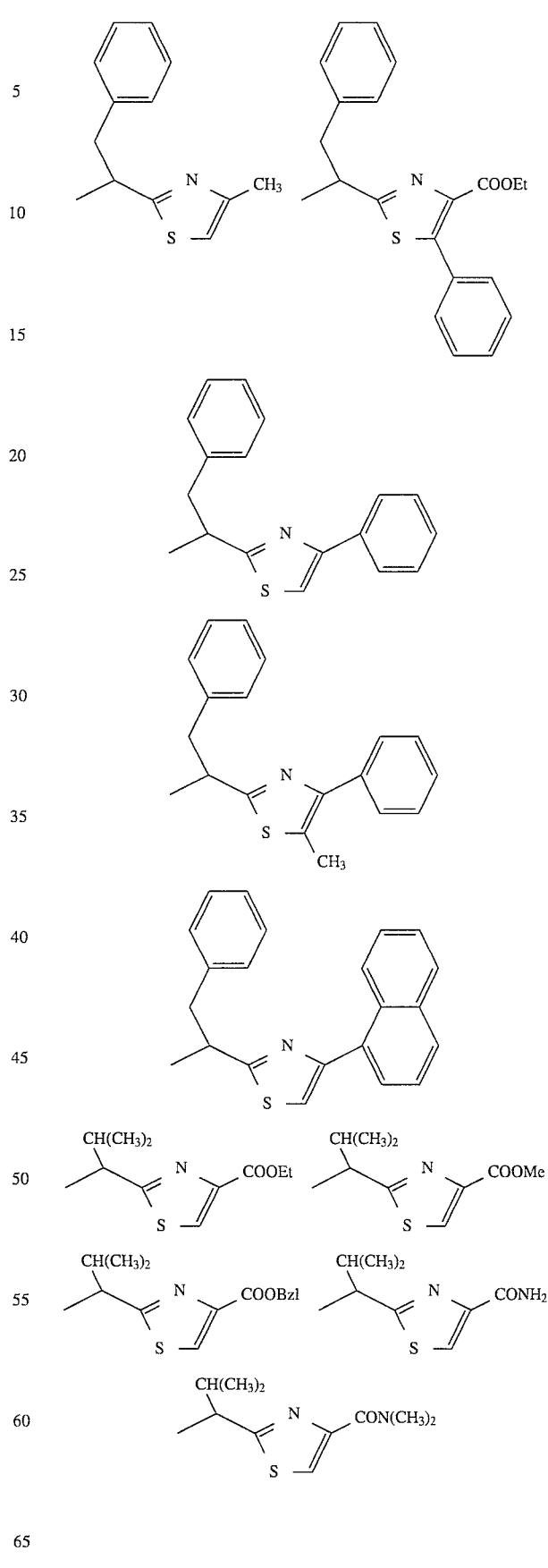

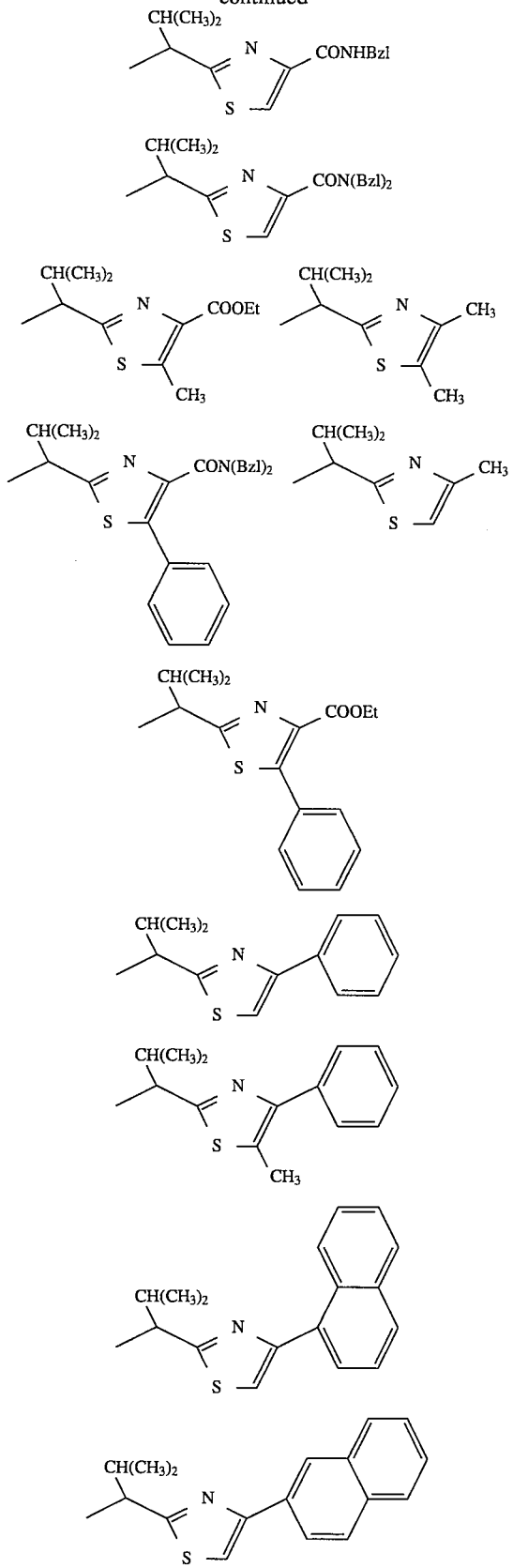
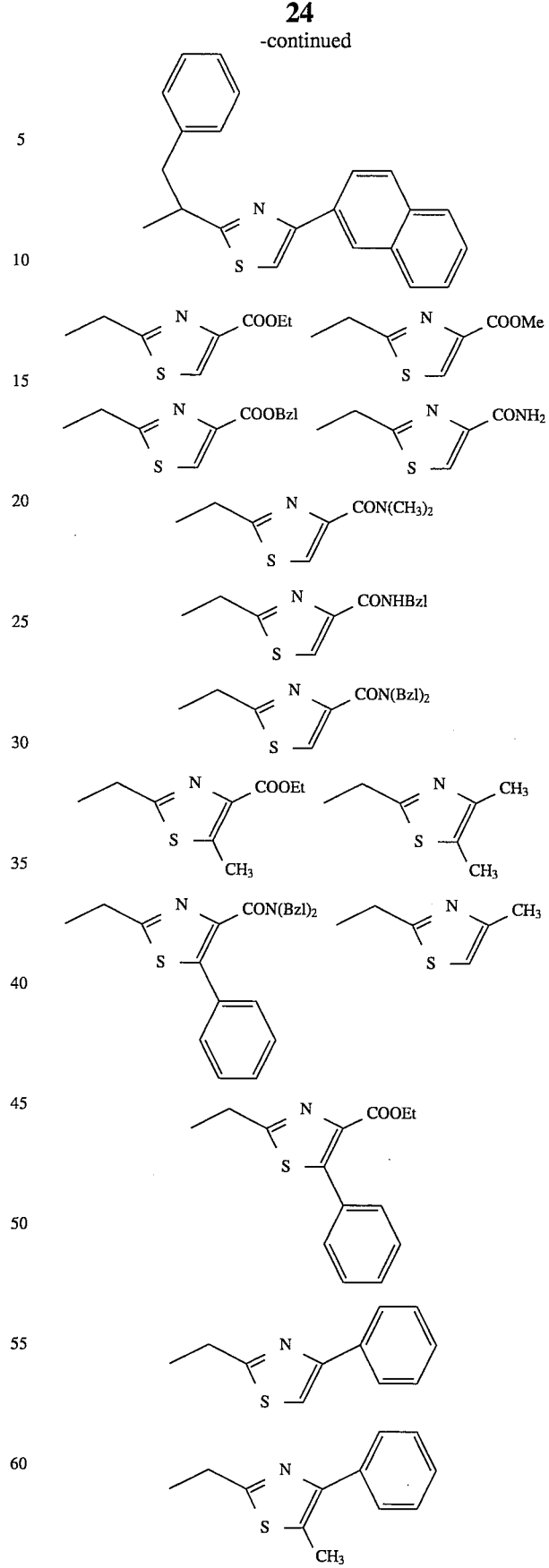

-continued
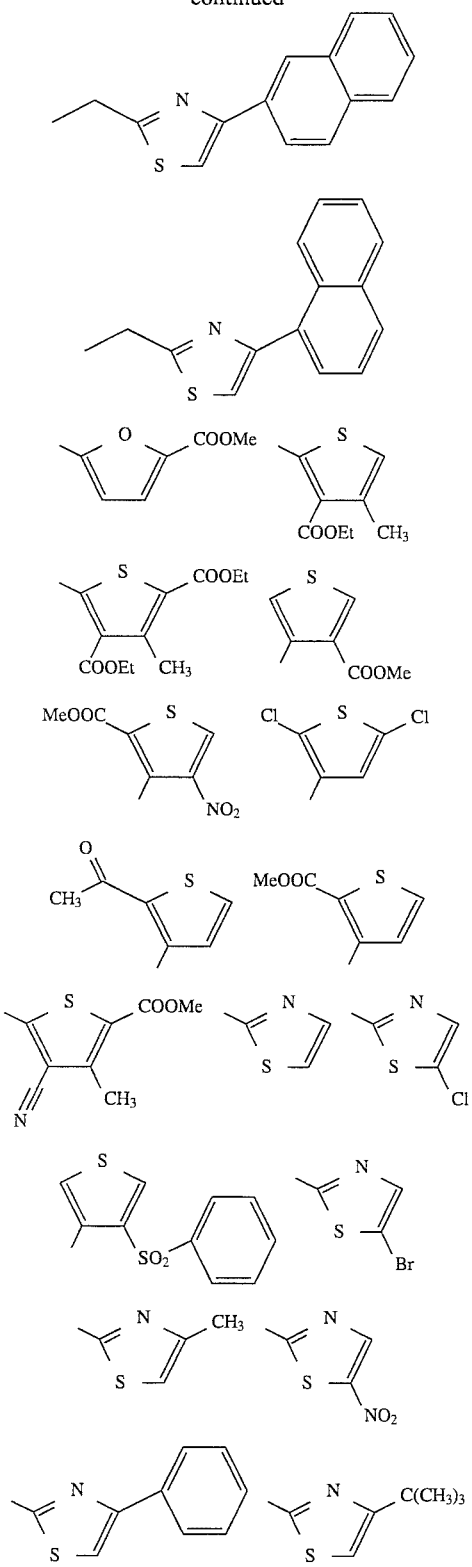
-continued
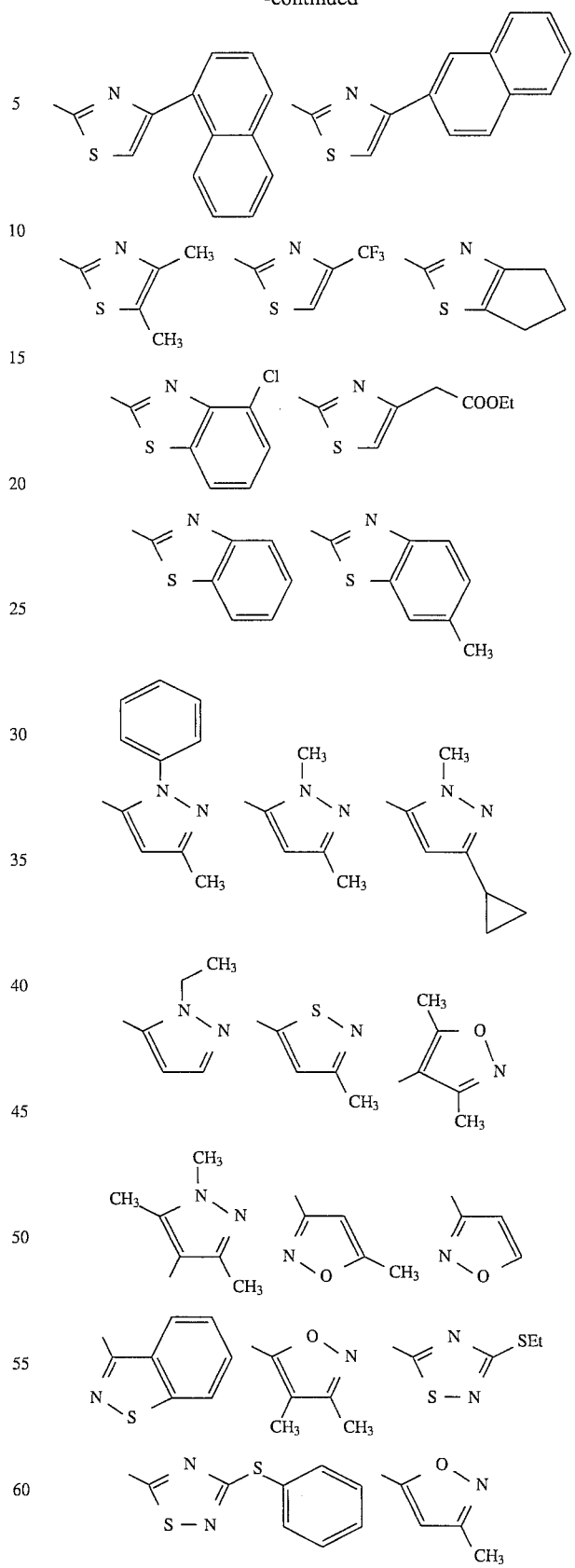

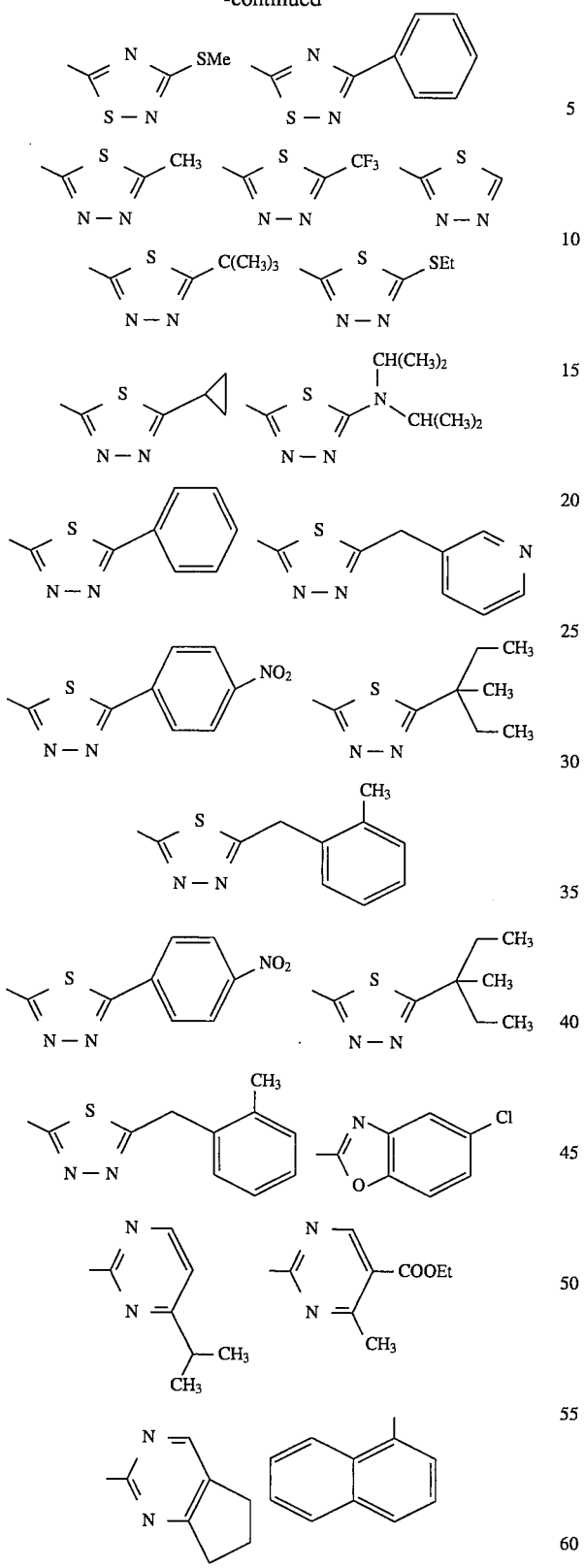
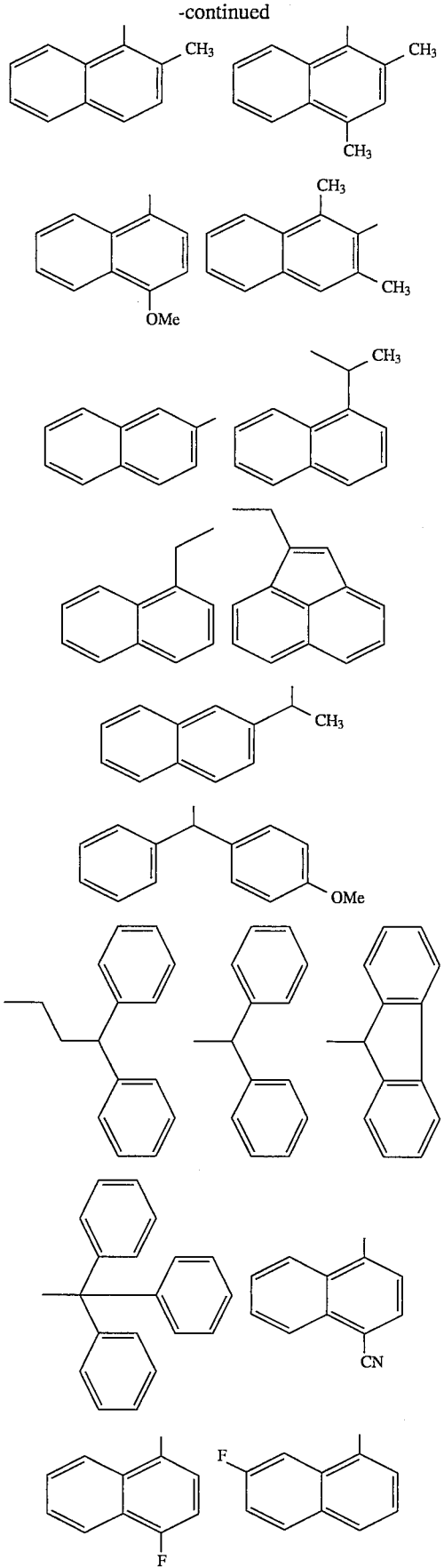

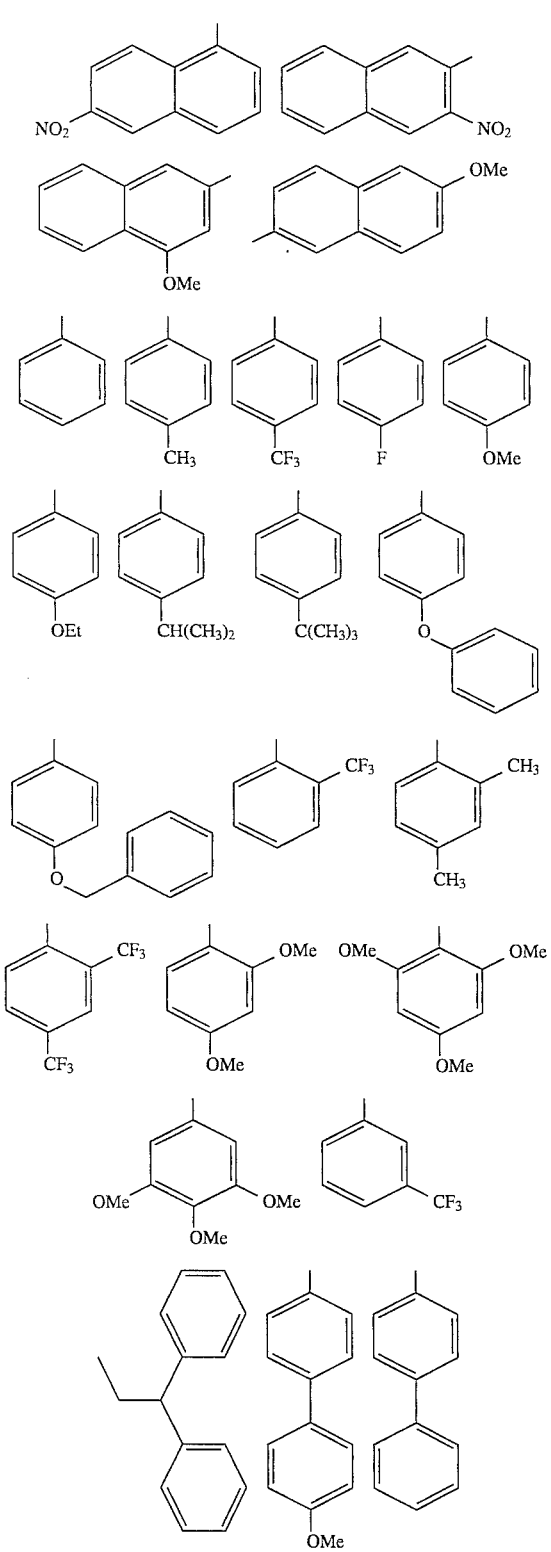
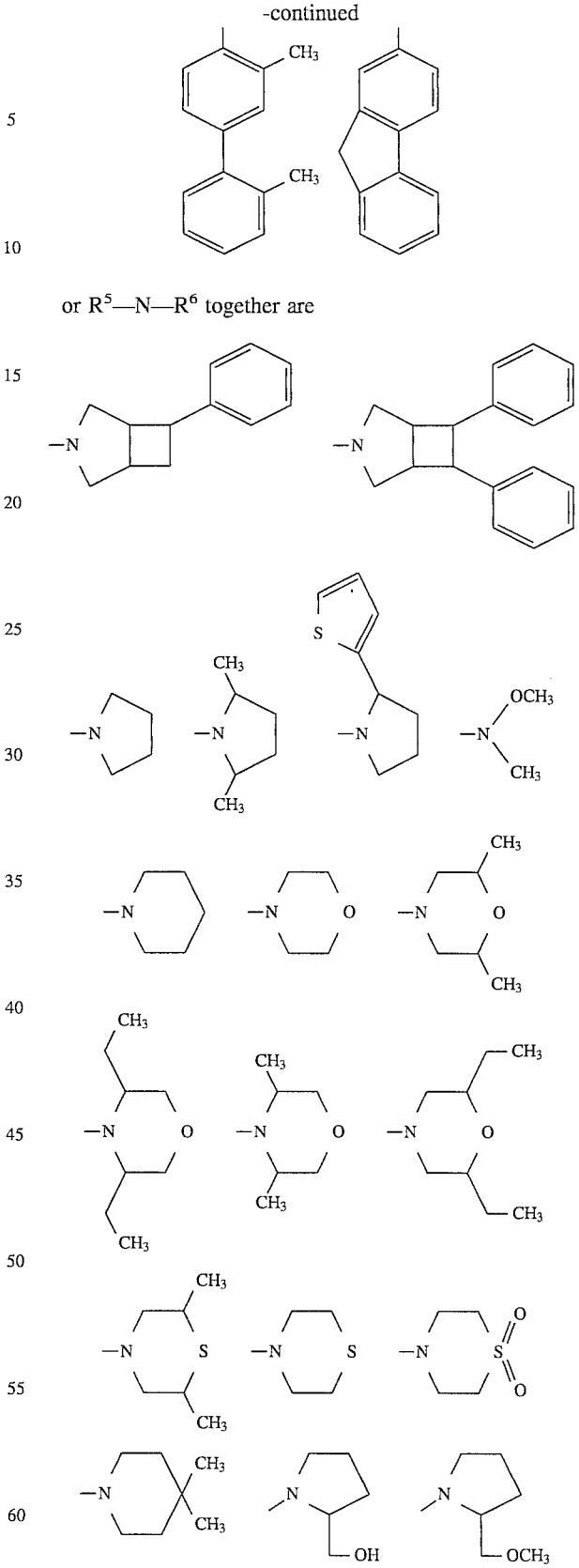
or $R^5$—N—$R^6$ together are

31
-continued
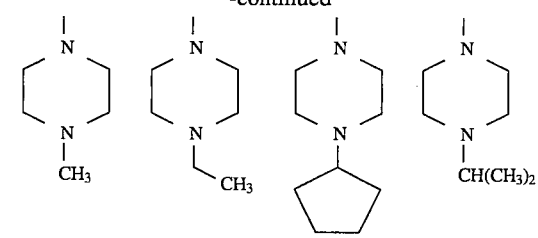
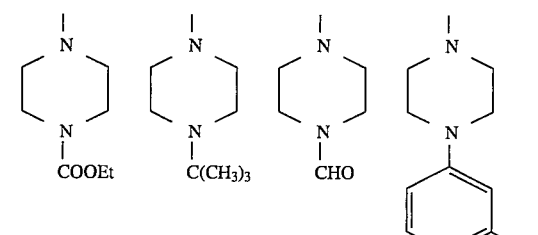
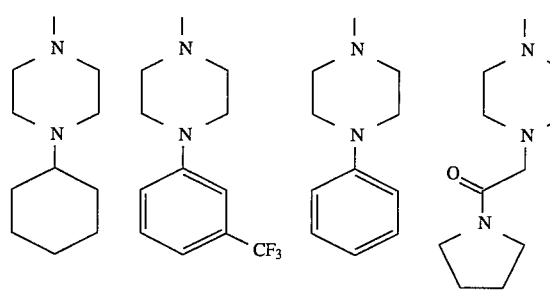
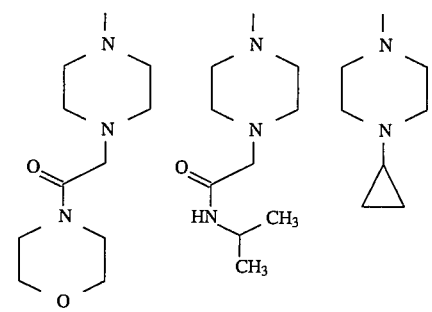
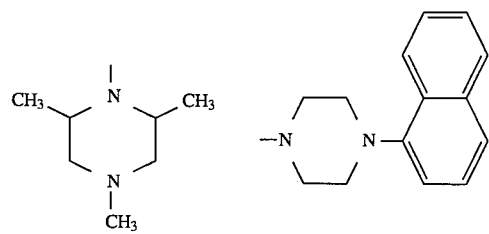
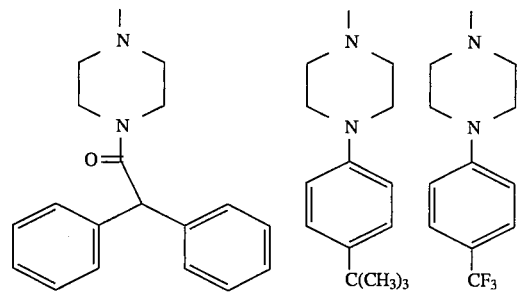
32
-continued
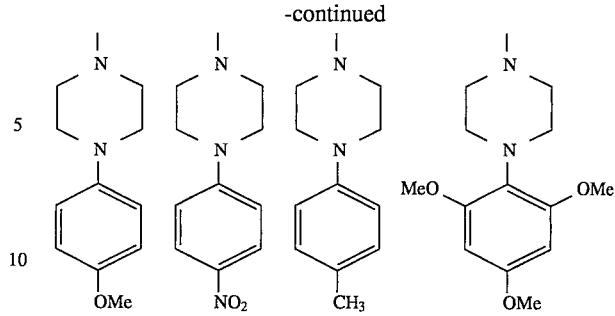
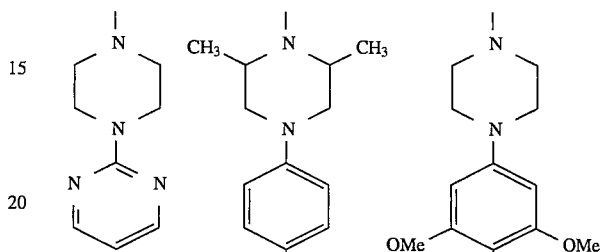
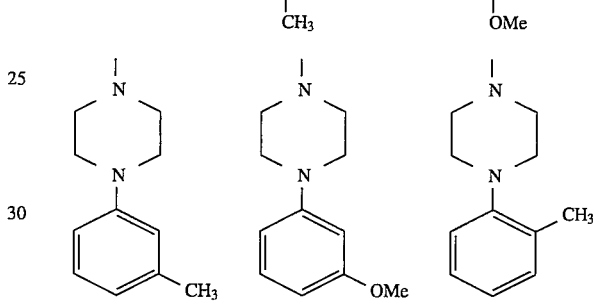
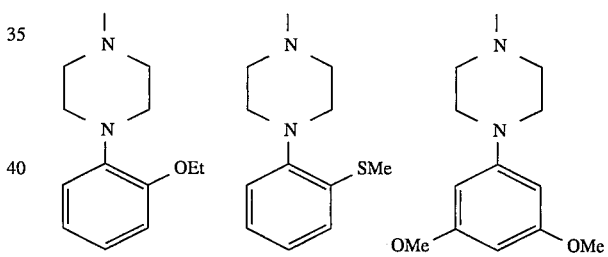
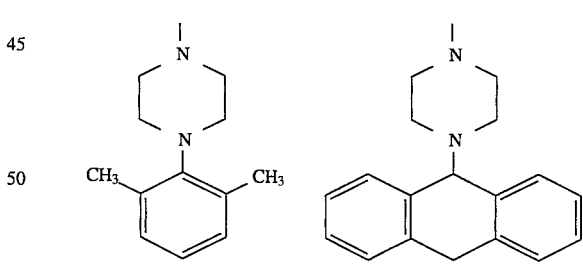
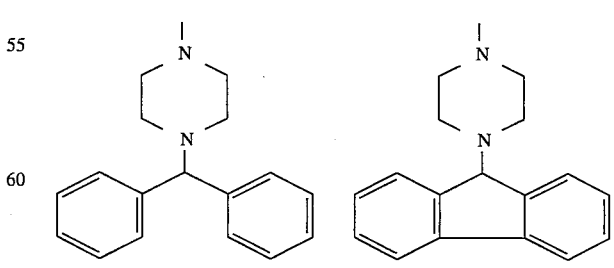

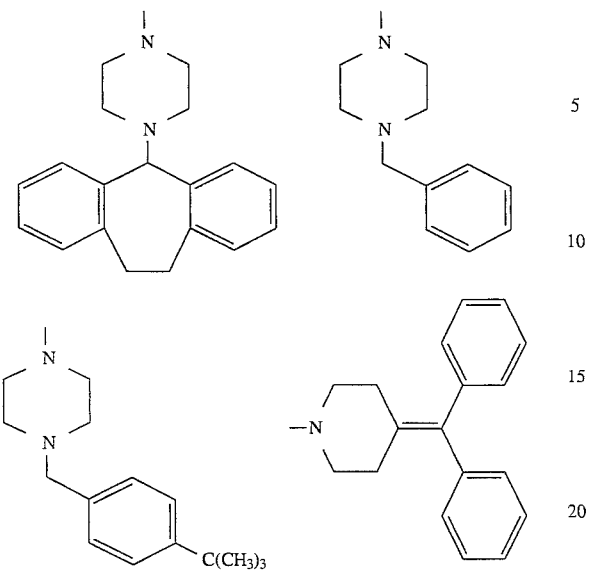

More preferred are compounds where the substituents have the following meanings:

R¹ is ethyl, methyl, trifluoroethyl, fluoroethyl, difluoroethyl, isopropyl, propyl, cyclopropyl, benzyloxycarbonyl, methyloxycarbonyl, lactyl, methylaminosulfonyl, tosyl, ureyl, mesyl, N(CH₃)₂, amidino or CH₃O—;

R² is H, methyl, ethyl, isopropyl, propyl, butyl, cyclopropyl, formyl, acetyl, propionyl, pivaloyl, benzoyl or benzyl; or R¹—N—R² together are

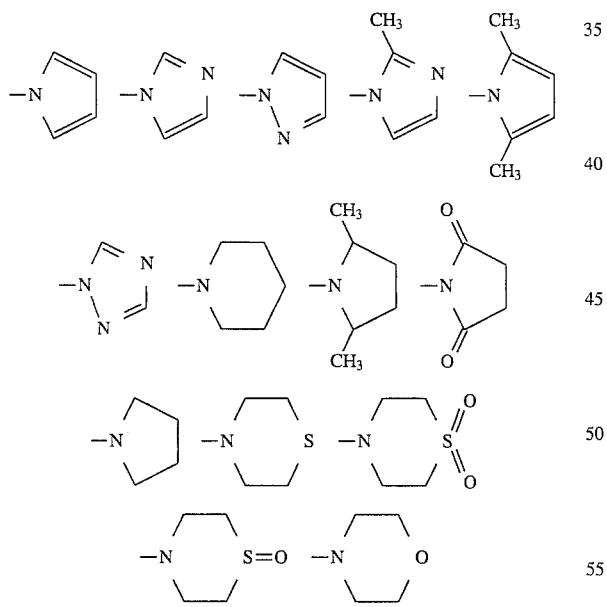

X is hydrogen, methyl, isopropyl, —CH₂CH(CH₃)₂, —CH(CH₃)CH₂CH₃, tert-butyl, or benzyl;

A is valyl, isoleucyl, leucyl, 2-tert-butylglycyl or 2-ethylglycyl;

R³ is hydrogen, methyl, or ethyl;

B is hydrogen, methyl, isopropyl, —CH₂CH(CH₃)₂, —CH(CH₃)CH₂CH₃, tert-butyl, or benzyl;

D is hydrogen, hydroxy, methoxy or tert-butyloxy;

E is hydrogen, methyl, isopropyl, tert-butyl, or ethyl; or

B and E together are —(CH₂)₃— or —(CH₂)₂—;

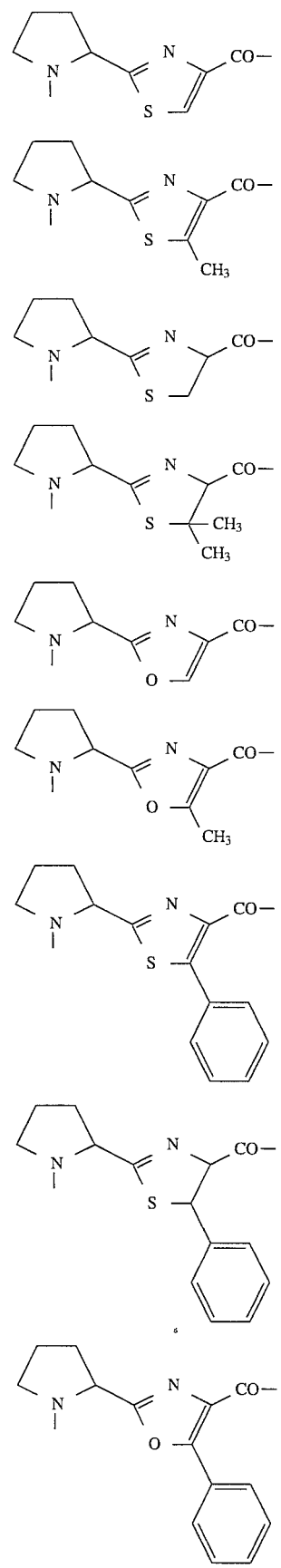

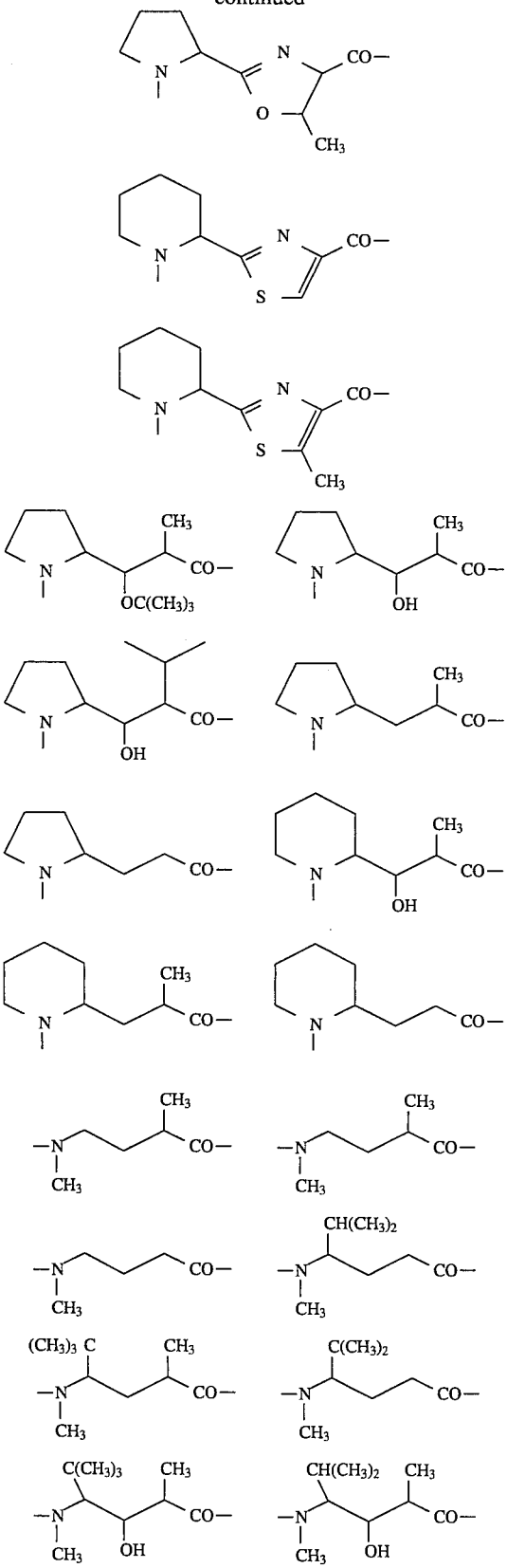
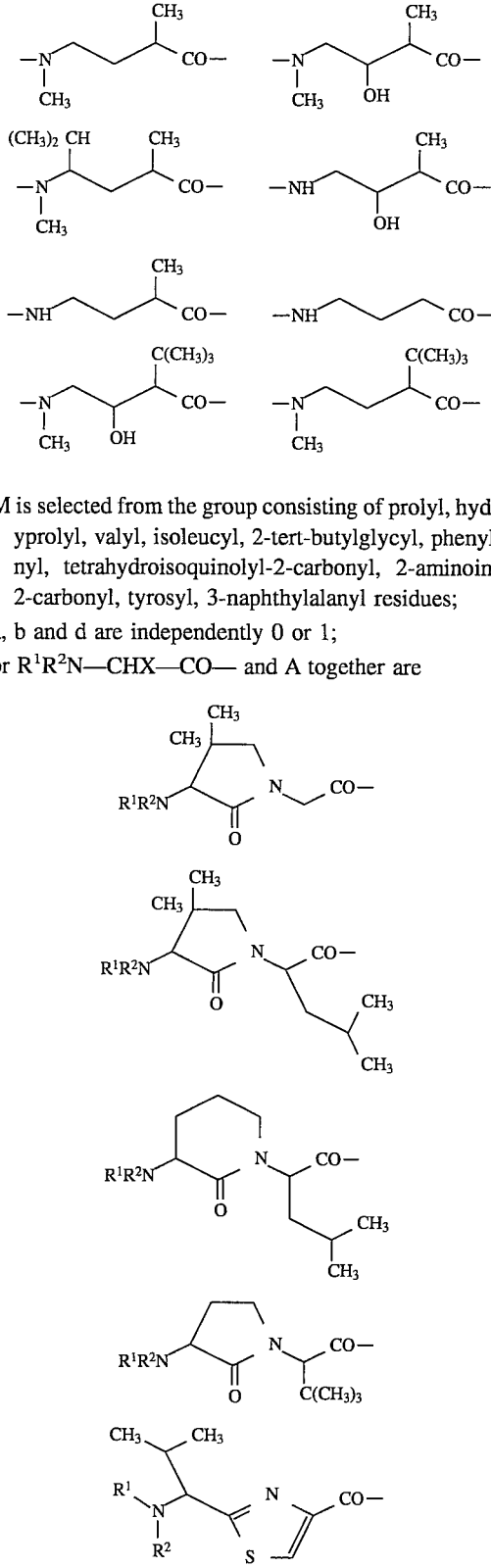
M is selected from the group consisting of prolyl, hydroxyprolyl, valyl, isoleucyl, 2-tert-butylglycyl, phenylalanyl, tetrahydroisoquinolyl-2-carbonyl, 2-aminoindyl-2-carbonyl, tyrosyl, 3-naphthylalanyl residues;
a, b and d are independently 0 or 1;
or $R^1R^2N$—CHX—CO— and A together are 37
-continued
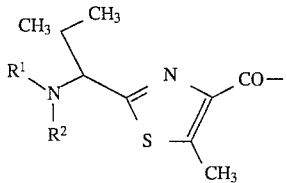
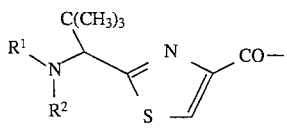
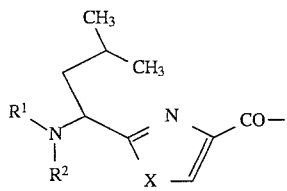
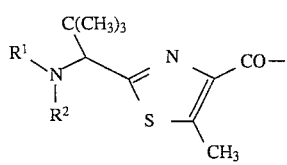
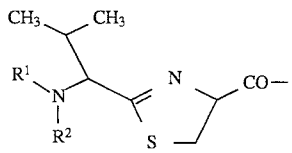
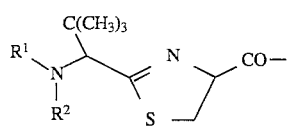
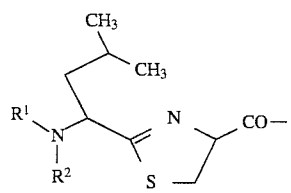
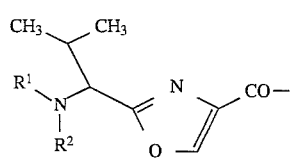
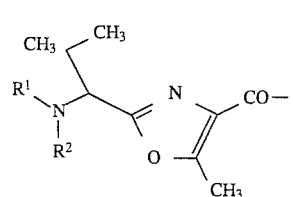
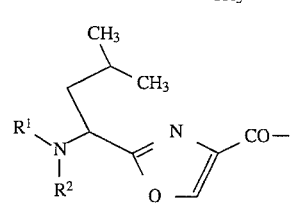
38
-continued
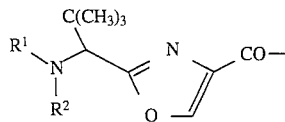
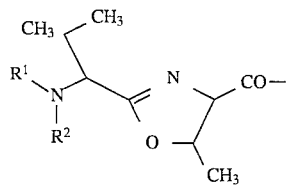
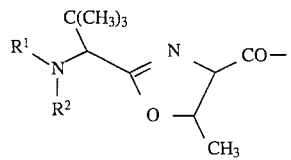
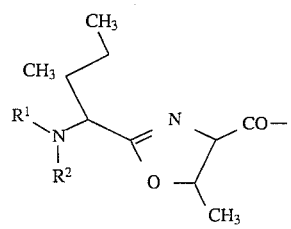
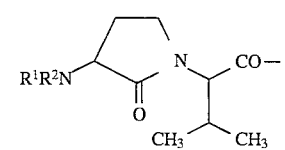
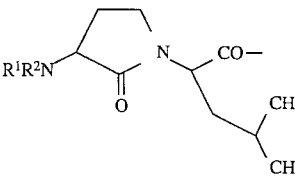
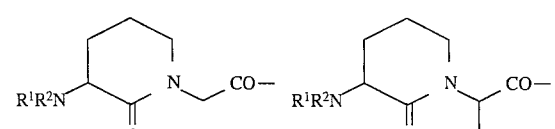
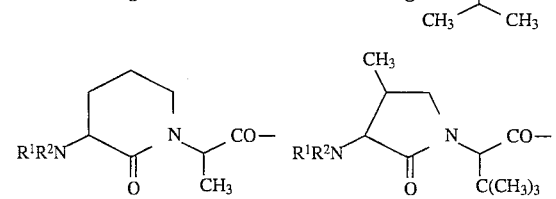
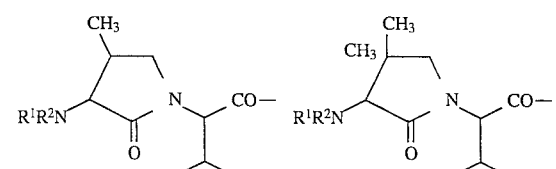

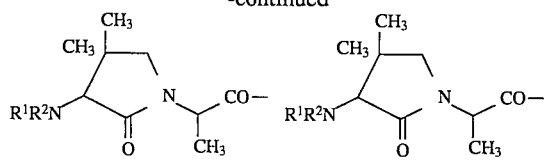

Q is a hydroxyl, $C_{1-4}$-alkoxyl, benzyloxyl or amino moiety $-NR^5R^6$
where
R⁵ is hydrogen, methyl, ethyl, trifluorethyl, fluoroethyl, difluoroethyl, propyl, isoproypyl, cyclopropyl, cyclopentyl, cyclohexyl;
R⁶ is hydrogen, methyl, ethyl, propyl, isopropyl, tert-butyl, benzyl, 4-phenoxybenzyl, 4-benzyloxybenzyl, 3,4,5-trimethoxybenzyl, phenyl, 4-phenoxyphenyl, 4-benzyloxyphenyl, 3,4,5-trimethoxyphenyl or

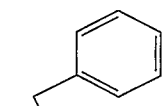
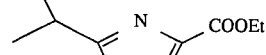
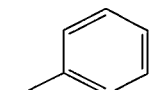
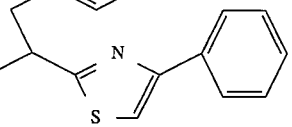
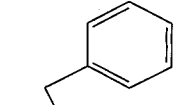
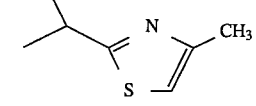
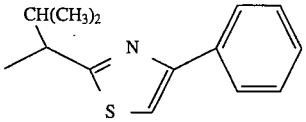
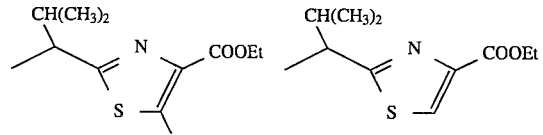
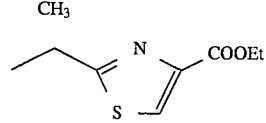
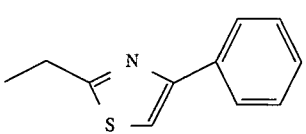

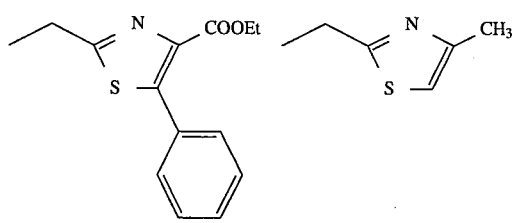
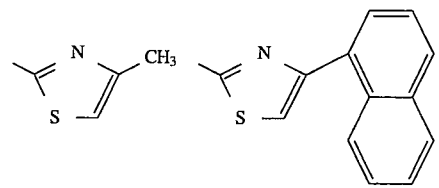
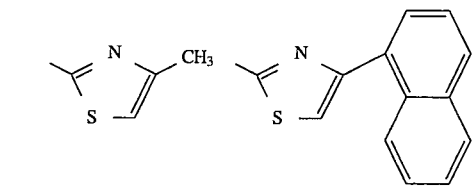
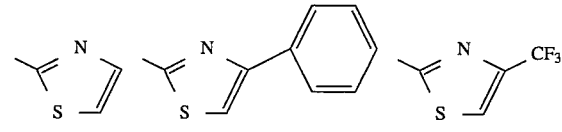
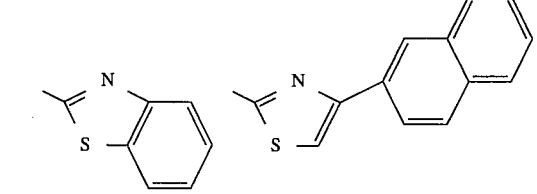
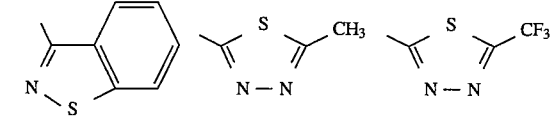
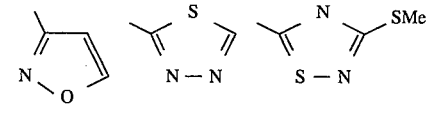
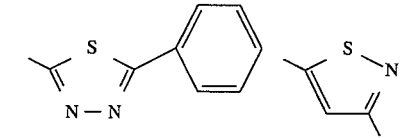
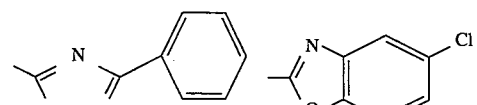
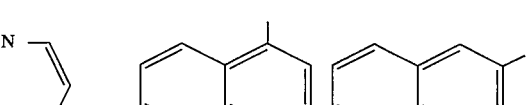
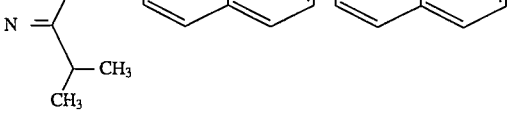

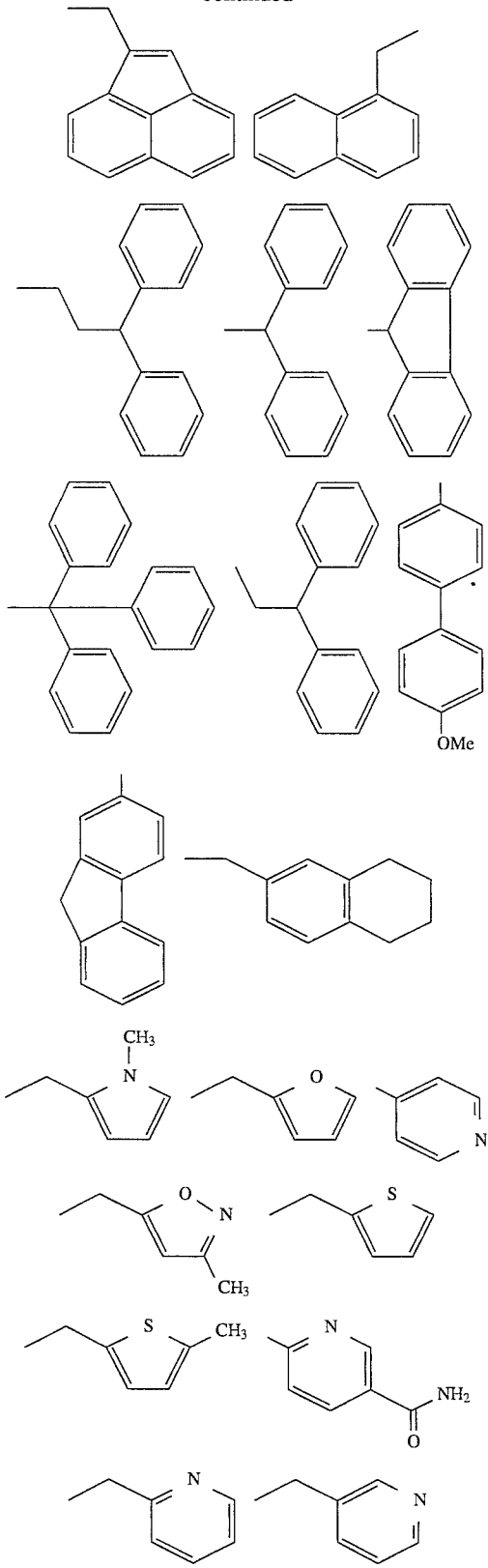
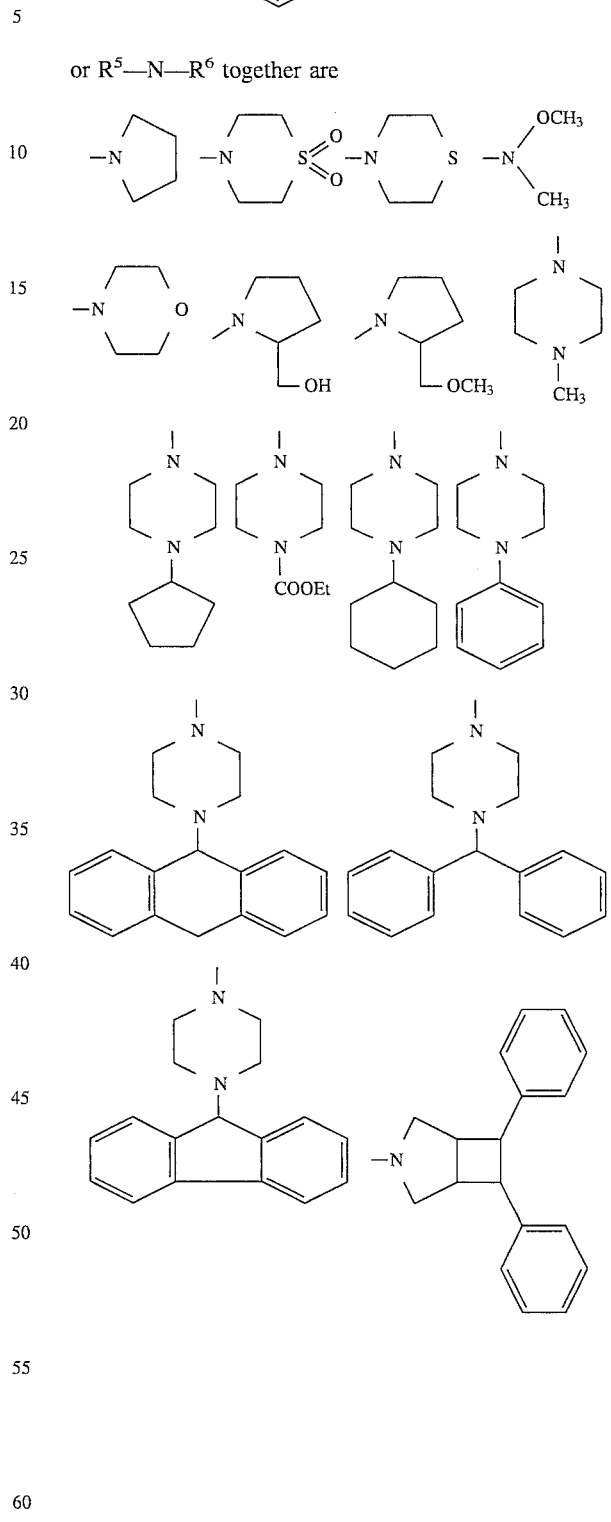
or R⁵—N—R⁶ together are

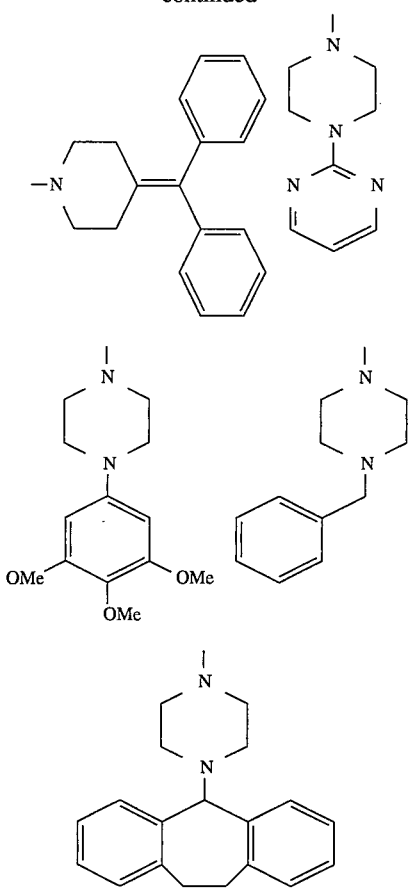

These examples illustrate but do not limit the scope of the present invention.

The compounds of the formula I are composed preferably of L-amino acids or components derived from L-amino acids but they may contain one or more D-amino acids or components derived from D-amino acids.

Particularly suitable physiologically tolerated acids are: hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The novel compounds can be prepared by known methods. Thus, the compounds can be assembled sequentially or by linking suitable small fragments. In the sequential assemblage, starting at the C terminus the peptide chain is extended stepwise by one amino acid or building block each time. In fragment coupling it is possible to link together fragments of different lengths, and the fragments in turn can be obtained by sequential assemblage from amino acids or building blocks.

Both in the sequential assemblage and in the fragment coupling it is necessary to link the units by forming an amide linkage. Enzymatic and chemical methods are suitable for this.

Chemical methods for forming the amide linkage are described in detail by Müller, Methoden der organischen Chemie Vol. XV/2, pp 1 to 364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976 and other standard works on peptide chemistry. Particular preference is given to the azide method, the symmetric and mixed anhydride method, in situ generated or preformed active esters, the use of urethane protected N-carboxy anhydrides of amino acids and the formation of the amide linkage using coupling reagents, especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)-carbodiimide hydrochloride (EDCI), n-propanephosphonic anhydride (PPA), N,N-bis(2-oxo-3-oxazolidinyl)-amidophosphoryl chloride (BOP-Cl), bromo-tris-pyrrolidinophosphoniumhexa-fluorophosphate (PyBrop), diphenylphosphoryl azide (DPPA), Castro's reagent (BOP, PyBop), O-benzotriazolyl-N,N,N',N'-tetramethyluronium salts (HBTU), diethylphosphoryl cyanide (DEPCN), 2,5-diphenyl-2,3-dihydro-3-oxo-4-hydroxythiophene dioxide (Steglich's reagent; HOTDO) and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu) or 2-hydroxypyridine.

Whereas it is normally possible to dispense with protective groups in enzymatic peptide synthesis, reversible protection of reactive groups not involved in formation of the amide linkage is necessary for both reactants in chemical synthesis. Three conventional protective group techniques are preferred for the chemical peptide syntheses: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, Methoden der organischen Chemie Vol. XV/1, pp 20 to 906, Thieme Verlag, Stuttgart, 1974. The units employed for assembling the peptide chain can be reacted in solution, in suspension or by a method similar to that described by Merrifield in J. Amer. Chem. Soc. 85 (1963) 2149. Particularly preferred methods are those in which peptides are assembled sequentially or by fragment coupling using the Z, Boc or Fmoc protective group technique, with one of the reactants in the said Merrifield technique being bonded to an insoluble polymeric support (also called resin hereinafter). This typically entails the peptide being assembled sequentially on the polymeric support using the Boc or Fmoc protective group technique, the growing peptide chain being covalently bonded at the C terminus to the insoluble resin particles (cf. FIGS. 1 and 2). This procedure makes it possible to remove reagents and byproducts by filtration, and thus recrystallization of intermediates is unnecessary.

The protected amino acids or building blocks can be linked to any suitable polymers, which merely have to be insoluble in the solvents used and to have a stable physical form which makes filtration easy. The polymer must contain a functional group to which the first protected amino acid can be firmly attached by a covalent bond. Suitable for this purpose are a wide variety of polymers, eg. cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl-resin (Pam-resin), p-benzyloxy-benzyl-alcohol-resin, benzhydryl-amine-resin (BHA-resin), 4-(hydroxymethyl)benzoyloxy-methyl-resin, the resin of Breipohl et al. (Tetrahedron Letters 28 (1987) 565; supplied by BACHEM), 4-(2,4-dimethoxyphenylaminomethyl)phenoxy-resin (supplied by Novabiochem) or o-chlorotrityl-resin (supplied by Biohellas).

Suitable for amide bond formation in solution are all solvents which are inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of the said solvents. Synthesis on the polymeric support can be carried out in all inert organic solvents in which the amino-acid derivatives used are soluble; however, preferred solvents additionally have resin-swelling properties, such as DMF, DCM, NMP, acetonitrile and DMSO, and mixtures of these solvents. After synthesis is complete, the compound is cleaved off the polymeric support. The conditions under which cleavage off the various resin types is possible are disclosed in the literature. The cleavage reactions most commonly used are acid- and palladium-catalyzed, especially cleavage in liquid anhydrous hydrogen fluoride, in anhydrous trifluoromethanesulfonic acid, in dilute or concentrated trifluoroacetic acid, palladium-catalyzed cleavage in THF or THF-DCM mixtures in the presence of a weak base such as morpholine or cleavage in acetic acid/dichloromethane/trifluoroethanol mixtures. Depending on the chosen protective groups, these may be retained or likewise cleaved of under the cleavage conditions. Partial deprotection of the peptide may also be worthwhile when certain derivatization reactions are to be carried out. Compounds dialkylated at the N-terminus can be prepared either by coupling of the appropriate N,N-dialkylamino acids in solution or on the polymeric support, by reductive alkylation in solution (with e.g. NaCNBH$_3$ in MeOH) or by reductive alkylation of the resin-bound compound in DMF/1% acetic acid with NaCNBH$_3$ and the appropriate aldehydes. Compounds with γ- or δ-lactam bridges can be prepared by incorporating the appropriate lactam-bridged dipeptide units (R. Freidinger, J. Org. Chem. (1982) 104–109) into the peptide chain. Compounds with thiazole-, oxazol-, thiazolin- or oxazolin-containing dipeptide building blocks can be prepared by incorporating the appropriate dipeptidic units (U. Schmidt et al., Synthesis (1987), 233–236; P. Jouin et al., Tetrahedron Letters (1992), 2807–2810; P. Wipf et al., Tetrahedron Letters (1992), 907–910; W. R. Tully, J. Med. Chem. (1991), 2065; Synthesis (1987), 235; T. Shioiri et. al., J. Org. Chem. (1987), 1252–1255; R. Pettit et al., J. Am. Chem. Soc. (1989), 5463–65) into the peptide chain. The building blocks having the structure —NR$^3$—CHB—CHD—CHE—CO— and —NR$^4$—CHG—CHK—CHL—CO— can be prepared according to the literature by reacting for example the corresponding protected amino acid aldehydes with the appropriate alkylating species like phosphonates, phosphorous ylides, Evans's reagent etc. (S. Shibuya et al., Heterocycles (1990), 1597–1600; M. Braun et al., Angew. Chem. (1987), 24–37; Angew. Chem. 1992, 104, No. 10; T. Shioiri et al., Peptide Chemistry 1989, N. Yanaihara (Ed.), 291–296; Pettit et al., J. Am. Chem. Soc. 1989, 111, 5463; T. Shioiri, Tetrahedron Letters 1991, 931–934; K. Koga, Tetrahedron Letters 1991, 2395–2398.

The compounds of this invention may be used to inhibit or otherwise treat solid tumors (e.g. tumors of the lung, breast, colon, prostate, bladder, rectum, or endometrial tumors) or hematological malignancies (e.g. leucemias, lymphomas) by administration of the compound to the mammal. Administration may be by any of the means which are conventional for pharmaceutical, preferably oncological, agents, including oral and parenteral means such as subcutaneously, intravenously, intramuscularly and intraperitoneally. The compounds may be administered alone or in the form of pharmaceutical compositions containing a compound of formula I together with a pharmaceutically accepted carrier appropriate for the desired route of administration. Such pharmaceutical compositions may be combination products, i.e., may also contain other therapeutically active ingredients.

The dosage to be administered to the mammal will contain an effective tumor-inhibiting amount of active ingredient which will depend upon conventional factors including the biological activity of the particular compound employed; the means of administration; the age, health and body weight of the recipient; the nature and extent of the symptoms; the frequency of treatment; the administration of other therapies; and the effect desired. A typical daily dose will be about 5 to 250 milligrams per kilogram of body weight on oral administration and about 1 to 100 milligrams per kilogram of body weight on parenteral administration.

Suitable dosage forms contain about 10 to 500 milligrams of active ingredient per unit. The active ingredient will thus ordinarily comprise about 1–90% by weight based on the total weight of the composition.

The novel compounds can be administered in conventional solid or liquid pharmaceutical administration forms, eg. uncoated or (film-)coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sucker et al.: Pharmazeutische Technologie, Thieme-Verlag, Stuttgart, 1978). The administration forms obtained in this way normally contain 1–90% by weight of the active substance.

The following examples are intended to illustrate the invention. The proteinogenous amino acids are abbreviated in the examples using the known three-letter code. Other meanings are: TFA=trifluoroacetic acid, Ac=acetic acid, Bu=butyl, Et=ethyl, Me=methyl, Bzl=benzyl, A. General Procedures I. The compounds claimed in claim 1 are either synthesized by classical solution synthesis using standard Z- and Boc-methodology as described above or by standard methods of solid-phase synthesis either manually or on a completely automatic model 431A synthesizer supplied by APPLIED BIOSYSTEMS. The different synthetic cycles for the Boc and Fmoc protective group techniques are as follows:

a) Synthetic cycle for the Boc protective group technique

| | | |
|---|---|---|
| 1. | 30% trifluoroacetic acid in DCM | 1 × 3 min |
| 2. | 50% trifluoroacetic acid in DCM | 1 × 1 min |
| 3. | DCM washing | 5 × 1 min |
| 4. | 5% diisopropylethylamine in DCM | 1 × 1 min |
| 5. | 5% diisopropylethylamine in NMP | 1 × 1 min |
| 6. | NMP washing | 5 × 1 min |
| 7. | Addition of preactivated protected amino acid (activation with 1 equivalent of DCC and 1 equivalent of HOBt in NMP/DCM); Peptide coupling (1st part) | 1 × 30 min |
| 8. | Addition of DMSO to the reaction mixture until it contains 20% DMSO by volume | |
| 9. | Peptide coupling (2nd part) | 1 × 16 min |
| 10. | Addition of 3.8 equivalents of diisopropylethylamine to the reaction mixture | |
| 11. | Peptide coupling (3rd part) | 1 × 7 min |
| 12. | DCM washing | 3 × 1 min |
| 13. | if conversion is incomplete, repetition of coupling (back to 5.) | |

| 14. | 10% acetic anhydride, 5% diisopropyl-ethylamine in DCM | 1 × 2 min |
| 15. | 10% acetic anhydride in DCM | 1 × 4 min |
| 16. | DCM washing | 4 × 1 min |
| 17. | back to 1. | |

BOP-Cl and PyBrop were used as reagents for coupling of the amino acid following N-methylamino acids or building blocks bearing an N-methyl group. The reaction times were correspondingly increased. In solution synthesis, the use of either Boc-amino acid-NCAs (N-tert.-butyloxycarbonyl-amino acid-N-carboxy-anhydrides) or Z-amino acid-NCAs (N-benzyloxycarbonyl-amino acid-N-carboxy-anhydrides) respectively is most advantageous for this type of coupling.

b) Synthetic cycle for the Fmoc protective group technique

| 1. | DMF washing | 1 × 1 min |
| 2. | 20% piperidine in DMF | 1 × 4 min |
| 3. | 20% piperidine in DMF | 1 × 16 min |
| 4. | DMF washing | 5 × 1 min |
| 5. | Addition of the preactivated protected amino acid (activation by 1 equivalent of TBTU and 1.5 equivalent of DIPEA in DMF); Peptide coupling | 1 × 61 min |
| 6. | DMF washing | 3 × 1 min |
| 7. | if conversion is incomplete, repetition of coupling (back to 5.) | |
| 8. | 10% acetic anhydride in DMF | 1 × 8 min |
| 9. | DMF washing | 3 × 1 min |
| 10. | back to 2 | |

BOP-Cl and PyBrop were used as reagents for coupling of the amino acid following the N-methylamino acid or building blocks bearing an N-methyl group. The reaction times were correspondingly increased.

II. Reductive alkylation of the N terminus

The peptide-resin prepared as in AIa or AIb was deprotected at the N terminus (steps 2–4 in AIb or 1–6 in AIa) and then reacted with a 3-fold molar excess of aldehyde or ketone in DMF/1% acetic acid with addition of 3 equivalents of NaCNBH$_3$. After reaction was complete (negative Kaiser test) the resin was washed several times with water, isopropanol, DMF and dichloromethane.

III. Workup of the peptide-resins obtained as in Ia and II

The peptide-resin was dried under reduced pressure and transferred into a reaction vessel of a TEFLON HF apparatus (supplied by PENINSULA). Addition of a scavenger, preferably anisole (1 ml/g of resin), and in the case of tryptophan-containing peptides of a thiol to remove the indolic formyl group, preferably ethanedithiol (0.5 ml/g of resin), was followed by condensing in hydrogen fluoride (10 ml/g of resin) while cooling with liquid N$_2$. The mixture was left to warm to 0° C. and stirred at this temperature for 45 min. The hydrogen fluoride was then stripped off under reduced pressure, and the residue was washed with ethyl acetate in order to remove remaining scavenger. The compound was extracted with 30% strength acetic acid and filtered, and the filtrate was lyophilized.

IV. Work-up of the peptide-resins obtained as in Ib and II

The peptide-resin was dried under reduced pressure and then subjected to one of the following cleavage procedures, depending on the amino-acid composition (Wade, Tregear, Howard Florey Fmoc Workshop Manual, Melbourne 1985).

| Cleavage conditions | | |
|---|---|---|
| TFA | Scavenger | Reaction time |
| 1 | 95% | 5% H$_2$O | 1.5 h |
| 2 | 95% | 5% ethanedithiol/anisol (1:3) | 1.5 h |

The suspension of the peptide-resin in the suitable TFA mixture was stirred at room temperature for the stated time and then the resin was filtered off and washed with TFA and DCM. The filtrate and the washings were concentrated, and the compound was precipitated by addition of diethyl ether. After cooling in an ice bath, the precipitate was filtered off, taken up in 30% acetic acid and lyophilized.

V. When an o-chlorotrityl-resin (supplied by Biohellas) is used, the suspension of the peptide-resin in an acetic acid/trifluoroethanol/dichloromethane mixture (1:1:3) is stirred at room temperature for 1 h. The resin is then filtered off with suction and thoroughly washed with the cleavage solution. The combined filtrates are concentrated in vacuo and treated with water. The precipitated solid is removed by filtration or centrifugation, washed with diethyl ether and dried under reduced pressure.

VI. Purification and characterization of the compounds

Purification was carried out by gel chromatography (SEPHADEX G-10, G-15/10% HOAc, SEPHADEX LH20/MeOH) with or without subsequent medium pressure chromatography (stationary phase: HD-SIL C-18, 20–45µ, 100 Å; mobile phase: gradient with A=0.1% TFA/MeOH, B=0.1% TFA/H$_2$O). The purity of the resulting products was determined by analytical HPLC (stationary phase: 100 2.1 mm VYDAC C-18, 5 1, 300 Å; mobile phase: CH$_3$CN/H$_2$O gradient, buffered with 0.1% TFA, 40° C.). Characterization was by fast atom bombardment mass spectroscopy and $^1$H- or $^{13}$C-spectroscopy.

B. Specific Procedures

EXAMPLE 1

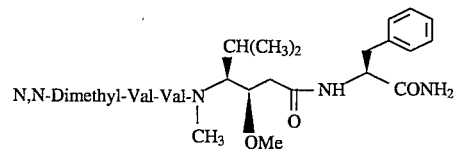

0.4 g phenylalaninamide hydrochloride (2 mmol) and 0.55 g Boc-N(CH$_3$)—CH[CH(CH$_3$)$_2$]— CH(OCH$_3$)—CH$_2$—COOH (2 mmol; synthesized according to the literature: S. Shibuya et al., Heterocycles, vol. 31) no. 9, 1597–1600 (1990) were dissolved in DMF. After addition of 0.4 g DEPCN (2.2 mmol) and 1.4 ml Diisopropylamine (DIPEA), the reaction mixture was stirred overnight at room temperature, the solvent evaporated under reduced pressure, and the residue taken up in ethylacetate and thoroughly washed with 5% aqueous citric acid, water, 5% NaHCO$_3$, and NaCl solution. The organic layer was dried over Na$_2$SO$_4$, filtered, and evaporated to dryness. The residue (0.66 g) was dried in vacuo, deprotected with 5 ml TFA/DCM (1:1) for 2 hours and evaporated to dryness. The thus obtained deprotected fragment was dissolved in DMF and reacted with 0.44 g N-tert.butyloxycarbonyl-valine-N-carboxyanhydride (1.8 mmol) at 45° C. After stirring for 5 h the solvent was evaporated in vacuo, ethylacetate added, and the organic layer washed thoroughly with 5% aqueous citric acid, 5% aqu. NaHCO₃, water, and aqu. NaCl, and dried over Na₂SO₄. The solvent was evaporated under reduced pressure and the residue (0.7 g, 1.3 mmol) treated with 5 ml TFA/DCM (1:1) for 2 h. After evaporation of the solvent mixture and drying over KOH, the residue was dissolved in DMF and 0.19 g N,N-dimethylvaline (1.3 mmol; synthesized according to the literature: see e.g. R. E. Bowmann, J. Chem. Soc. 1959, 1342), 0.25 g DEPCN (1.5 mmol) and 0.7 ml DIPEA were added. The reaction mixture was stirred overnight at room temperature, evaporated to dryness and chromatographed on a SEPHADEX LH-220 column. Product fractions were collected and the solvent evaporated, yielding 0.46 g of compound 1.

EXAMPLE 2

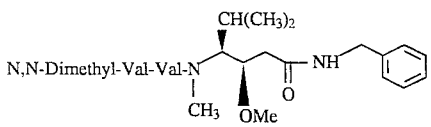

0.29 g benzylamine (2 mmol) and 0.55 g Boc-N(CH₃)—CH[CH(CH₃)₂]—CH(OCH₃)— CH₂—COOH (2 mmol; synthesized according to the literature: S. Shibuya et al., Heterocycles, vol. 31, no. 9, 1597–1600 (1990)) were dissolved in DMF. After addition of 0.4 g DEPCN (2.2 mmol) and 1.4 ml DIPEA, the reaction mixture was stirred overnight at room temperature, the solvent evaporated under reduced pressure, and the residue taken up in ethylacetate and thoroughly washed with 5% aqu. citric acid, water, 5% NaHCO₃, and NaCl solution. The organic layer was dried over Na₂SO₄, filtered, and evaporated to dryness. The residue (0.51 g) was dried in vacuo, deprotected with 5 ml TFA/DCM (1:1) for 2 hours and evaporated to dryness. The thus obtained deprotected fragment was dissolved in DMF and reacted with 0.4 g N-tert.-butyloxycarbonyl-valine-N-carboxyanhydride (1.6 mmol) at 45° C. After stirring for 5 h the solvent was evaporated in vacuo, ethylacetate added, and the organic layer washed thoroughly with 5% aqu. citric acid, 5% aqu. NaHCO₃, water, and aqu. NaCl, and dried over Na₂SO₄. The solvent was evaporated under reduced pressure and the residue (0.51 g, 1.1 mmol) treated with 5 ml TFA/DCM (1:1) for 2 h. After evaporation of the solvent mixture and drying over KOH, the residue was dissolved in DMF and 0.16 g N,N-dimethylvaline (1.1 mmol), 0.23 g DEPCN (1.4 mmol) and 0.7 ml DIPEA were added. The reaction mixture was stirred overnight at room temperature, evaporated to dryness and chromatographed on a SEPHADEX LH-20 column. Product fractions were collected and the solvent evaporated, yielding 0.36 g of compound 1.

The following compounds were prepared and can be prepared according to examples 1 and 2:
3. Xaa Val Xdm Xcx Xab
4. Xaa Val Xdm Xcx Xac
5. Xaa Val Xdm Xcx Xat
6. Xaa Val Xdm Xcx Xbp
7. Xaa Val Xdm Xcx Xbt
8. Xaa Val Xdm Xcx Xbu
9. Xaa Val Xdm Xcx Xbv
10. Xaa Val Xdm Xcx Xbw
11. Xaa Val Xdm Xcx Xby
12. Xaa Val Xdm Xcx Xca
13. Xaa Val Xdh Xcx Xbq
14. Xaa Val Xdh Xcx Xbs
15. Xaa Val Xdm Xat
16. Xaa Val Xdm Xbp
17. Xav Val Xdm Xbq
18. Xav Val Xdm Xbs
19. Xbo Val Xdm Xbt
20. Xbo Val Xdm Xbu
21. Xaa Vaf Xdm Xbv
22. Xaa Vaf Xdm Xbw
23. Xav Leu Xdm Xby
24. Xaa Leu Xdm Xca
25. Xaa Val Xdm Xcx Xcf
26. Xaa Val Xdm Xcx Xao
27. Xax Val Xdm NH₂
28. Xax Val Xdm Xcf
29. Xax Val Xdm Xao
30. Xaa Xdm NH₂
31. Xax Xdm NH₂
32. Xaa Xdm Xcf
33. Xax Xdm Xcf
34. Xaa Xdm Phe Xcf
35. Xax Xdm Phe Xcf
36. Xaa Val Xda Xda NH₂
37. Xaa Val Xda Xda Phe NH₂
38. Xaa Val Xdh Xdh NH₂
39. Xaa Val Xdh Xdh Phe NH₂
40. Xaa Val Xda NH₂
41. Xaa Val Xdb NH₂
42. Xaa Val Xdc NH₂
43. Xaa Val Xdd NH₂
44. Xaa Val Xde NH₂
45. Xaa Val Xdf NH₂
46. Xaa Val Xdg NH₂
47. Xaa Val Xdh NH₂
48. Xaa Val Xdi NH₂
49. Xaa Val Xdk NH₂
50. Xaa Val Xdl NH₂
51. Xaa Val Xdn NH₂
52. Xaa Val Xdo NH₂
53. Xaa Val Xdp NH₂
54. Xaa Val Xdq NH₂
55. Xaa Val Xdm Xcx NH₂
56. Xaa Val Xdm Xcy NH₂
57. Xaa Val Xdm Xcz NH₂
58. Xaa Val Xdm Xds NH₂
59. Xaa Val Xdm Xcw NH₂
60. Xaa Val Xdm Xda NH₂
61. Xaa Val Xar NH₂
62. Xaa Val Xdm Xdc NH₂
63. Xaa Val Xdm Xbf NH₂
64. Xaa Val Xdm Xbg NH₂
65. Xaa Val Xdm Xck
66. Xaa Val Xdm Xcl
67. Xaa Val Xdm Xcx Phe NH₂
68. Xaa Val Xdm Xcx Phe Xcf
69. Xaa Val Xdm Xcx Phe Xao
70. Xaa Val Xdm Xcx Xad NH₂
71. Xaa Val Xdm Pro NH₂
72. Xaa Val Xdm Xcx Xdr NH₂
73. Xaa Val Xdm Xcx Xcu NH₂
74. Xav Val Xdm Xcx Phe NH₂
75. Xax Val Xdm Xcx Phe NH₂
76. Xaa Val Xdm Phe NH₂
77. Xav Val Xdm Phe NH₂
78. Xax Val Xdm Phe NH₂
79. Xas Val Xdm Phe NH₂
80. Xaa Val Xdm Xab
81. Xaa Val Xdm Xac
82. Xbh Xdm NH₂

83. Xbi Xdm Xcx NH₂
84. Xbk Xdm Xcx Phe NH₂
85. Xbl Xdh NH₂
86. Xbm Xdh Xcx NH₂
87. Xbn Xdh Xcx Phe NH₂
88. Xaa Xdm Phe NH₂
89. Xas Xdm Phe Xao
90. Xav Xdm Phe Xcf
91. Xax Xdm Phe NH₂
92. Xaa Val Xdm OH
93. Xaa Val Xdm OBzl
94. Xaa Val Xdm NH₂
95. Xaa Val Xdm Xan
96. Xaa Val Xdm Xao
97. Xaa Val Xdm Xap
98. Xaa Val Xdm Xau
99. Xaa Val Xdm Xaq
100. Xaa Val Xar Pro NH₂
101. Xaa Val Xdm Xbz
102. Xaa Val Xdm Xcb
103. Xaa Val Xdm Xcc
104. Xaa Val Xdm Xcd
105. Xaa Val Xdm Xce
106. Xaa Val Xdm Xcf
107. Xaa Val Xdm Xcg
108. Xaa Val Xdm Xch
109. Xaa Val Xdm Xci
110. Xaa Val Xdm Xcm
111. Xaa Val Xdm Xcn
112. Xaa Val Xdm Xco
113. Xaa Val Xdm Xcp
114. Xaa Val Xdm Xcq
115. Xaa Val Xdm Xcr
116. Xaa Val Xdm Xao
117. Xag Val Xdm NH₂
118. Xah Val Xdm NH₂
119. Xag Val Xdm NH₂
120. Xai Val Xdm NH₂
121. Xak Xaf Xdm NH₂
122. Xal Xaf Xdm NH₂
123. Xam Xaf Xdm NH₂
124. Xas Xaf Xdm NH₂
125. Xav Xaf Xdm NH₂
126. Xaw Val Xdm NH₂
127. Xax Val Xdm NH₂
128. Xay Val Xdm NH₂
129. Xaz Val Xdm NH₂
130. Xba Xaf Xdm Xcf
131. Xbb Xaf Xdm Xcf
132. Xbc Val Xdm NH₂
133. Xbd Val Xdm NH₂
134. Xbe Val Xdm NH₂
135. Xbo Xaf Xdm NH₂
136. Xcs Xaf Xdm NH₂
137. Xct Val Xdm NH₂
138. Xcv Val Xdm NH₂
139. Xaa Val Xdt Xcx Phe NH₂
140. Xaa Val Xdt Xcx NH₂
141. Xaa Val Xdt NH₂
142. Xaa Val Xdu Xcx NH₂
143. Xaa Val Xdu NH₂
144. Xdv Val Xdm Xcf
145. Xdw Val Xdm Xcf
146. Xdx Val Xdm Xcf
147. Xaa Val Xar Xae
148. Xaa Val Xar Xdy

TABLE I

Sequence Identification of Compounds Prepared According to Examples 1 and 2.

| Compound Number(s) | Sequence ID Number |
|---|---|
| 3–14, 25–26, 70, 72, 73 | 1 |
| 15–20, 28–29, 36, 38, 55–60, 62–66, 80–81, 95–99, 101–116, 140, 142, 144–148 | 2 |
| 21–22, 131 | 3 |
| 23–24 | 4 |
| 37, 39, 67–69, 74–75, 139 | 5 |
| 34–35, 89–90 | 6 |
| 76–79 | 7 |
| 84, 87 | 8 |
| 71, 100 | 9 |

The symbols Xaa . . . in the summary have the following meanings:

Xaa: N,N-Dimethylvaline

Xab: 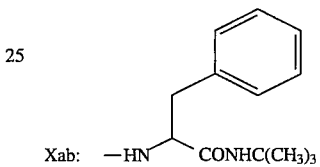

Xac: 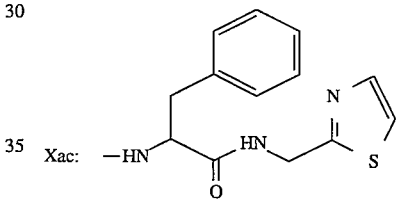

Xad: Tetrahydroisoquinoline carboxylic acid

Xae: 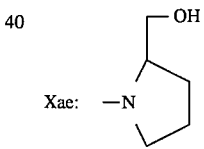

Xaf: tert-Leucine or 2-tert-butylglycine

Xag: N-N-Dimethylisoleucine

Xah: N,N-Dimethylleucine

Xai: N,N-Dimethyl-tert-leucine

Xak: N-amidino-valine

Xal: N-Acetyl-N-methylvaline

Xam: N-Methyl-N-benzylvaline

Xan: 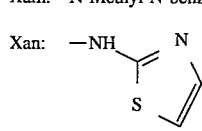

Xao: 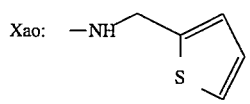

Xap: 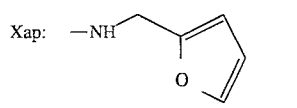
Xaq: 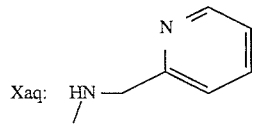
Xar: 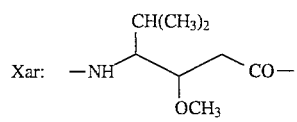
Xas: N-Methyl-N-isopropylvaline
Xat: 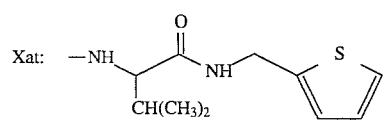
Xau: 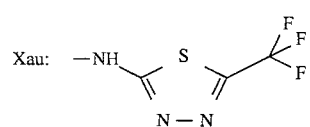
Xav: N,N-Diethylvaline
Xaw: N-Fluoroethylvaline
Xax: N,N-Dipropylvaline
Xay: N-Cyclopropylvaline
Xaz: 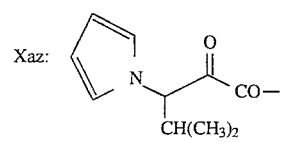
Xba: 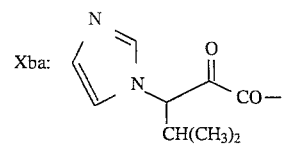
Xbb: 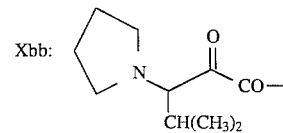
Xbc: 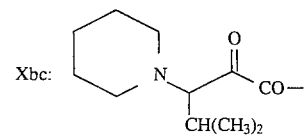
Xbd: 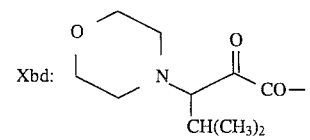
Xbe: 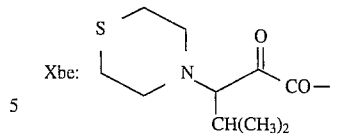
Xbf: 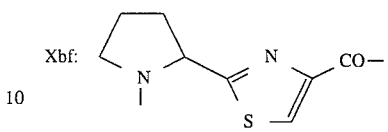
Xbg: 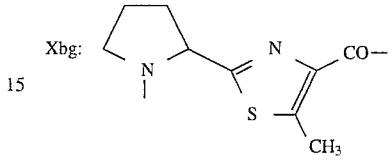
Xbh: 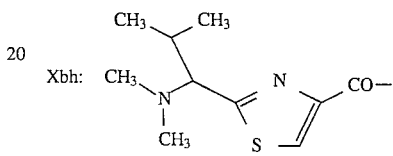
Xbi: 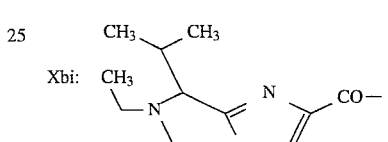
Xbk: 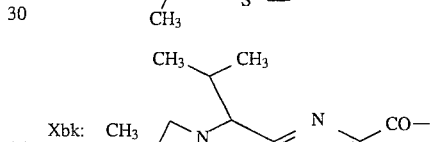
Xbl: 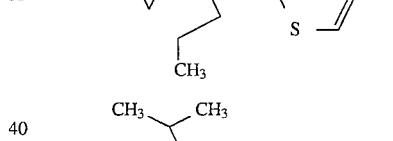
Xbm: 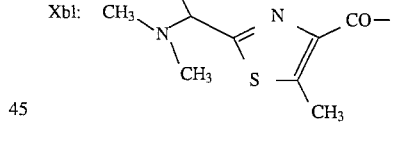
Xbn: 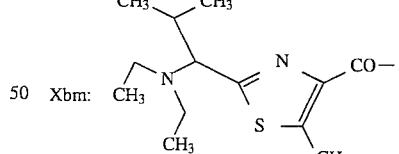
Xbo: N,N-Dipropyl-tert-leucine

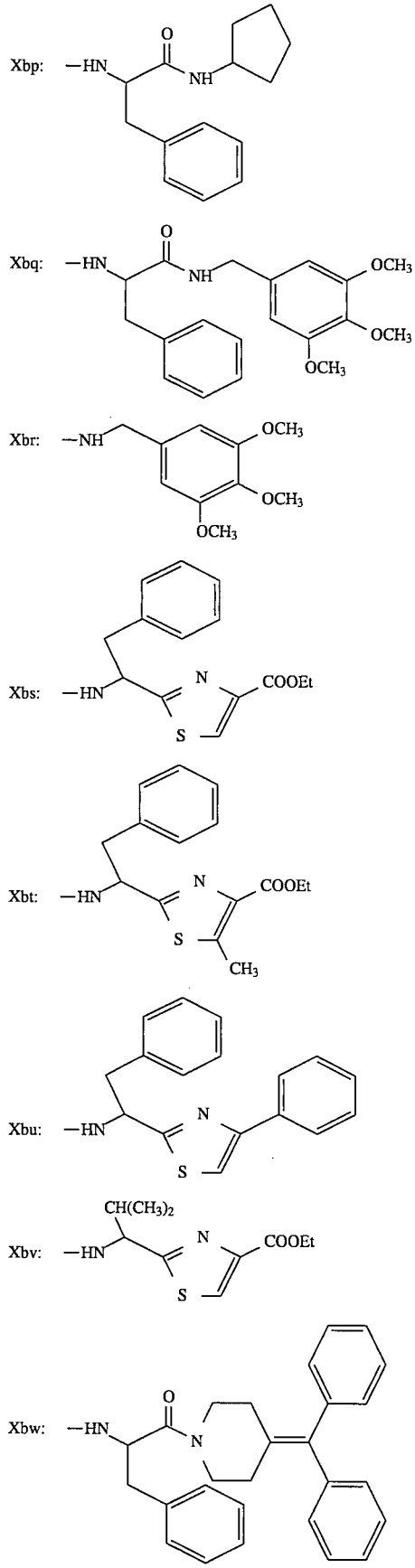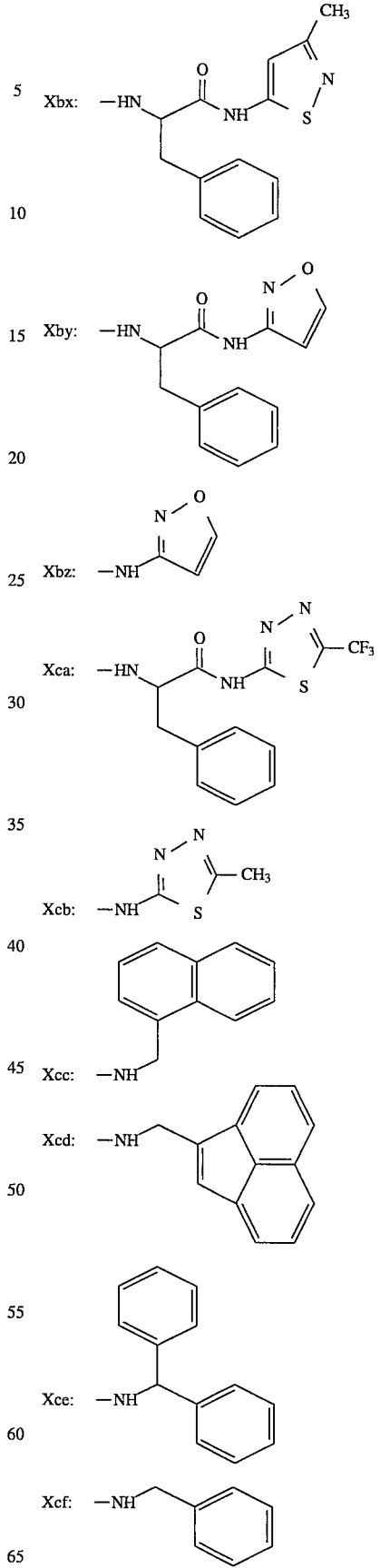

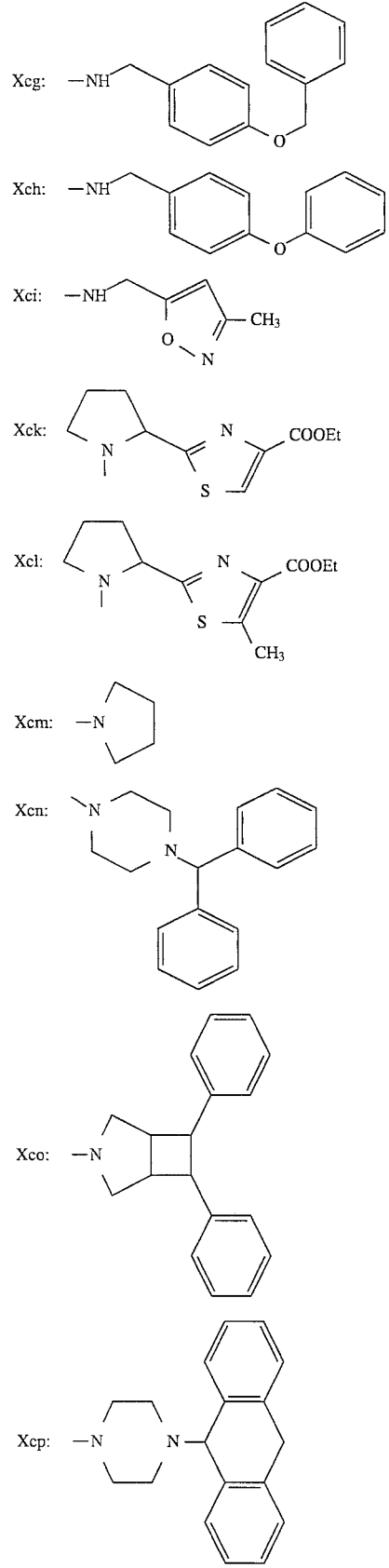
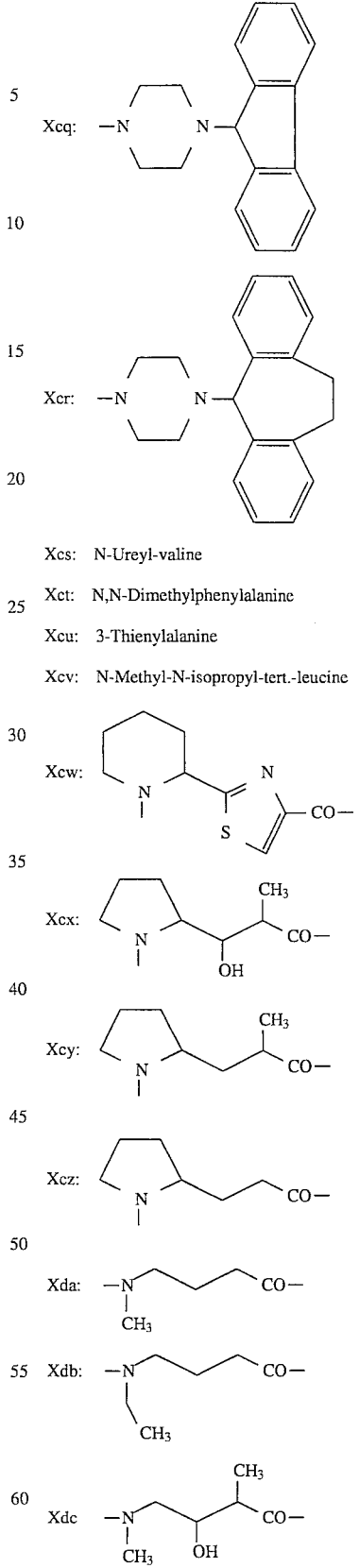
Xcs: N-Ureyl-valine
Xct: N,N-Dimethylphenylalanine
Xcu: 3-Thienylalanine
Xcv: N-Methyl-N-isopropyl-tert.-leucine

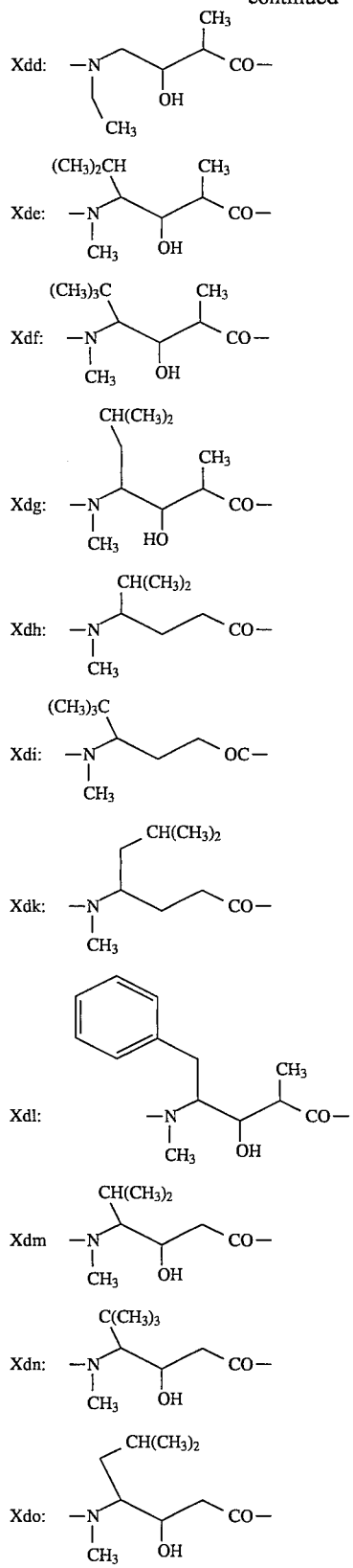
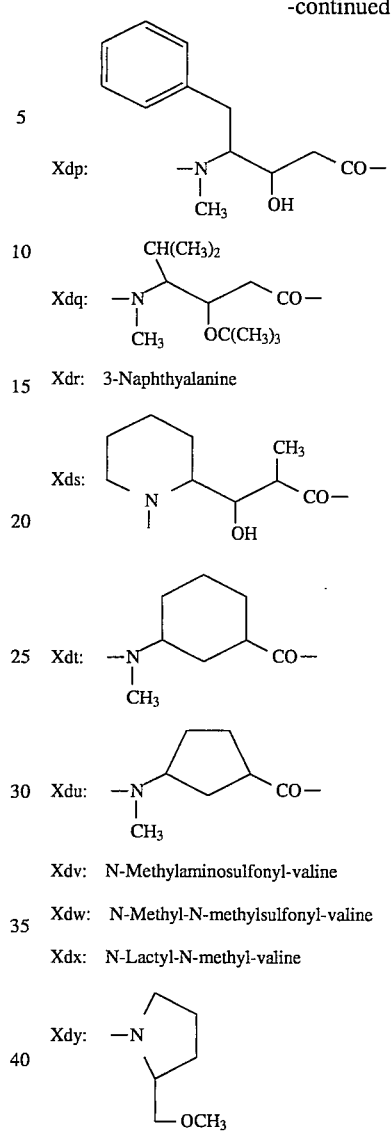

The ending —NH₂ means that the C-terminal amino acid or building block is in the amide form.

Compounds of this invention may be assayed for anti-cancer activity by conventional methods, including for example, the methods described below.

A. In vitro methodology

Cytotoxicity may be measured using a standard methodology for adherent cell lines such as the microculture tetrazolium assay (MTT). Details of this assay have been published (Alley, MC et al, Cancer Research 48:589–601, 1988). Exponentially growing cultures of tumor cells such as the HT-29 colon carcinoma or LX-1 lung tumor are used to make microtiter plate cultures. Cells are seeded at 5000–20,000 cells per well in 96-well plates (in 150 μl or media), and grown overnight at 37° C. Test compounds are added, in 10-fold dilutions varying from $10^{-4}$M to $10^{-10}$M. Cells are then incubated for 48 hours. To determine the number of viable cells in each well, the MTT dye is added (50 μl of 3 mg/ml solution of 3-(4,5-dimethylthiazol-2-yl)-2,5-diphenyltetrazolium bromide in saline). This mixture is incubated at 37° C. for 5 hours, and then 50 μl of 25% SDS, pH2 is added to each well. After an overnight incubation, the absorbance of each well at 550 nm is read using an ELISA reader. The values for the mean +/− SD of data from replicated wells are calculated, using the formula % T/C (% viable cells treated/control).

$$\frac{OD \text{ of treated cells}}{OD \text{ of control cells}} \times 100 = \% \ T/C$$

The concentration of test compound which gives a T/C of 50% growth inhibition was designated as the $IC_{50}$.

B. In vivo methodology

Compounds of this invention may be further tested in any of the various pre-clinical assays for in vivo activity which are indicative of clinical utility. Such assays are conducted with nude mice into which tumor tissue, preferably of human origin, has been transplanted ("xenografted"), as is well known in this field. Test compounds are evaluated for their anti-tumor efficacy following administration to the xenograft-bearing mice.

More specifically, human tumors which have been grown in athymic nude mice are transplanted into new recipient animals, using tumor fragments which are about 50 mg in size. The day of transplantation is designated as day 0. Six to ten days later, mice are treated with the test compounds given as an intravenous or intraperitoneal injection, in groups of 5–10 mice at each dose. Compounds were given daily for 5 days, 10 days or 15 days, at doses from 10–100 mg/kg body weight. Tumor diameters and body weights were measured twice weekly. Tumor volumes are calculated using the diameters measured with Vernier calipers, and the formula:

$$(length \times width^2)/2 = mg \text{ of tumor weight}$$

Mean tumor weights are calculated for each treatment group, and T/C values determined for each group relative to the untreated control tumors.

---

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Xaa  Val  Xaa  Xaa  Xaa
 1                    5
```

( 2 ) INFORMATION FOR SEQ ID NO: 2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Xaa  Val  Xaa  Xaa
 1
```

( 2 ) INFORMATION FOR SEQ ID NO: 3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 3:

```
Xaa  Xaa  Xaa  Xaa
 1
```

( 2 ) INFORMATION FOR SEQ ID NO: 4:

( i ) SEQUENCE CHARACTERISTICS:

( A ) LENGTH: 4 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 4:

Xaa Leu Xaa Xaa
 1

( 2 ) INFORMATION FOR SEQ ID NO: 5:

( i ) SEQUENCE CHARACTERISTICS:
                    ( A ) LENGTH: 5 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 5:

Xaa Val Xaa Xaa Phe
 1               5

( 2 ) INFORMATION FOR SEQ ID NO: 6:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 6:

Xaa Xaa Phe Xaa
 1

( 2 ) INFORMATION FOR SEQ ID NO: 7:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 7:

Xaa Val Xaa Phe
 1

( 2 ) INFORMATION FOR SEQ ID NO: 8:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 8:

Xaa Xaa Xaa Phe
 1

( 2 ) INFORMATION FOR SEQ ID NO: 9:

( i ) SEQUENCE CHARACTERISTICS:
                    ( A ) LENGTH: 6 amino acids
                    ( B ) TYPE: amino acid
                    ( D ) TOPOLOGY: linear ( i i ) MOLECULE TYPE: peptide ( x i ) SEQUENCE DESCRIPTION: SEQ ID NO: 9:

Xaa Val Xaa Xaa Phe Xaa
1               5

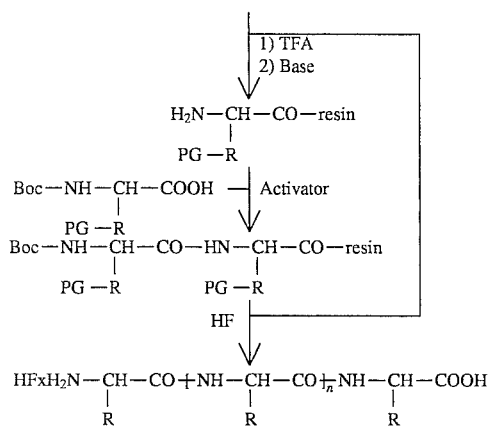

Boc=t-butyloxycarbonyl protective group
PG=side-chain protective group
R=amino-acid side chain

We claim:

1. A peptide of the formula I

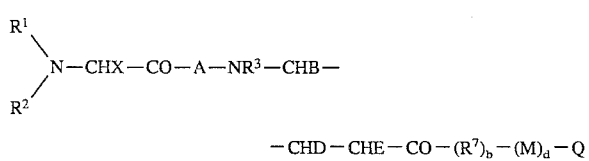

where
R$^1$ is methyl, ethyl, isopropyl, cyclopropyl or fluoroethyl;
R$^2$ is hydrogen, methyl, ethyl, isopropyl or cyclopropyl, or
R$^1$—N—R$^2$ together are

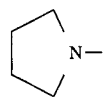

which may be unsubstituted or substituted by one or more methyl groups,
X is hydrogen, C$_1$–C$_5$-alkyl, cyclopropyl, cyclopentyl, cyclohexyl, —CH$_2$-cyclohexyl or benzyl;
A is valyl, isoleucyl, leucyl, allo-isoleucyl, 3-tert-butylalanyl, 2-tert-butylglycyl, 2-ethylglycyl or 2-cyclohexylglycyl;
R$^3$ is hydrogen, methyl or ethyl;
B is hydrogen, C$_1$–C$_5$-alkyl, cycloalkyl, —CH$_2$-cyclohexyl or benzyl;
D is hydrogen, hydroxy, acetoxy, or C$_1$–C$_4$-alkoxy;
E is hydrogen or C$_1$–C$_4$-alkyl;
R$^7$ is NR$^4$—CHG—CHK—CHL—CO—;
R$^4$ is hydrogen or methyl;
G is hydrogen, C$_1$–C$_5$-alkyl, cyclohexyl, —CH$_2$-cyclohexyl, or benzyl;
K is hydrogen, hydroxy, acetoxy, or C$_1$–C$_4$-alkoxy;

L is hydrogen, or C$_1$–C$_5$-alkyl, or
R$^4$ and G together are —(CH$_2$)$_4$—, —(CH$_2$)$_3$—, or —CH$_2$—CH(OH)—CH$_2$—;
M is valyl, 2-tert-butylglycyl, prolyl, hydroxyprolyl, isoleucyl, leucyl, 3-cyclohexylalanyl, phenylalanyl, tetrahydroisoquinolyl-2-carbonyl, 3-thiazolylalanyl, 3-thienylalanyl, histidyl, tyrosyl, 3-pyridylalanyl, 3-tert-butylalanyl, 2-cyclohexylglycyl, or 3-naphthylalanyl;
b and d are independently 0 or 1;
Q is hydroxy, C$_1$–C$_5$-alkoxy, phenoxy, benzyloxy or a substituted or unsubstituted amino group;
and the salts thereof with physiologically tolerated acids.

2. Compounds of formula I according to claim 1 wherein R$^1$—N—R$^2$ is a 5-membered heterocycle of the formula

which may be unsubstituted or substituted with one or more alkyl groups.

3. Compounds of formula I according to claim 1 wherein Q is an amino moiety of the formula R$^5$—N—R$^6$ wherein
R$^5$ is H, or hydroxy, or C$_{1-7}$-alkoxy, or benzyloxy, or C$_{1-7}$-alkyl, or fluoroethyl, or difluoroethyl, or trifluoroethyl, or C$_{3-7}$-cycloalkyl,
R$^6$ is H, or C$_{1-7}$-alkyl, or phenyl (which may be substituted by up to three substituents which may independently be CF$_3$, nitro, halogen, CONHBzl, CON(Bzl)$_2$, C$_{1-4}$-alkyl which may form a cyclic system, C$_{1-4}$-alkoxy, phenoxy, benzoxy, of C$_{1-7}$-alkyl-sulfonyl), or
benzyl (which may be substituted by up to three substituents which may independently be CF$_3$, nitro, halogen, CONHBzl, CON(Bzl)$_2$, C$_{1-4}$-alkyl which may form a cyclic system, C$_{1-4}$-alkoxy, phenoxy, benzoxy, or C$_{1-7}$-alkyl-sulfonyl), or naphthyl (which may be substituted by up to two substituents which may independently be CF$_3$, nitro, halogen, CONHBzl, CON(Bzl)$_2$, C$_{1-4}$-alkyl, C$_{1-4}$-alkoxy, benzoxy, phenoxy, or C$_{1-7}$-alkyl-sulfonyl), or
benzhydryl (which may be substituted by up to two substituents which may independently be CF$_3$, nitro, halogen, CONHBzl, CON(Bzl)$_2$, C$_{1-4}$-alkyl, C$_{1-4}$-alkoxy, phenoxy, benzoxy, or C$_{1-7}$-alkyl-sulfonyl), or
biphenyl (which may be substituted by up to two substituents which may independently be CF$_3$, nitro, halogen, CONHBzl, CON(Bzl)$_2$, C$_{1-4}$-alkyl, C$_{1-4}$-alkoxy, phenoxy, benzoxy, or C$_{1-7}$-alkyl-sulfonyl), or
triphenylmethyl (which may be substituted by up to three substituents which may independently be CF$_3$, nitro, halogen, CONHBzl, CON(Bzl)$_2$, C$_{1-4}$-alkyl, C$_{1-4}$-alkoxy, phenoxy, benzoxy, or C$_{1-7}$-alkyl-sulfonyl), or
benzhydrylethyl (which may be substituted by up to two substituents which may independently be CF$_3$, nitro, halogen, CONHBzl, CON(Bzl)$_2$, C$_{1-4}$-alkyl, $C_{1-4}$-alkoxy, phenoxy, benzoxy, or $C_{1-7}$-alkyl-sulfonyl), or benzhydrylmethyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or naphthylmethyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or acenaphthyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or acenaphthylmethyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or pyridyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or picolyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or benzothiazolyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or benzisothiazolyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or benzopyrazolyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or benzoxazolyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or fluorenyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or aminofluorenyl (which may be substituted by up to two substituents which may independently be $CF_3$, nitro, halogen, CONHBzl, CON(Bzl)$_2$, $C_{1-4}$-alkyl, $C_{1-4}$-alkoxy, phenoxy, benzoxy, or $C_{1-7}$-alkyl-sulfonyl), or pyrimidyl (which may be substituted by up to two substituents which may independently be $CF_3$, nitro, halogen, COOEt, CONHBzl, CON(Bzl)$_2$, $C_{1-4}$-alkyl which may form a cyclic system, $C_{1-4}$-alkoxy, phenoxy, benzoxy, or $C_{1-7}$-alkyl-sulfonyl), or 5-membered hetaryl, or —CHR$^7$-5-membered hetaryl (which may be substituted by up to two substituents which may independently be $CF_3$, nitro, halogen, CONHBzl, CON(Bzl)$_2$, COOMe, COOEt, COOCH(CH$_3$)$_2$, CONH$_2$, COOBzl, $C_{1-4}$-alkyl, $C_{1-4}$-alkoxy, phenoxy, benzoxy, phenyl, benzyl, naphthyl, or $C_{1-7}$-alkyl-sulfonyl).

4. Compounds of formula I according to claim 1 wherein Q is an amino moiety of the formula R$^5$—N—R$^6$, which forms a structure selected from the group consisting of

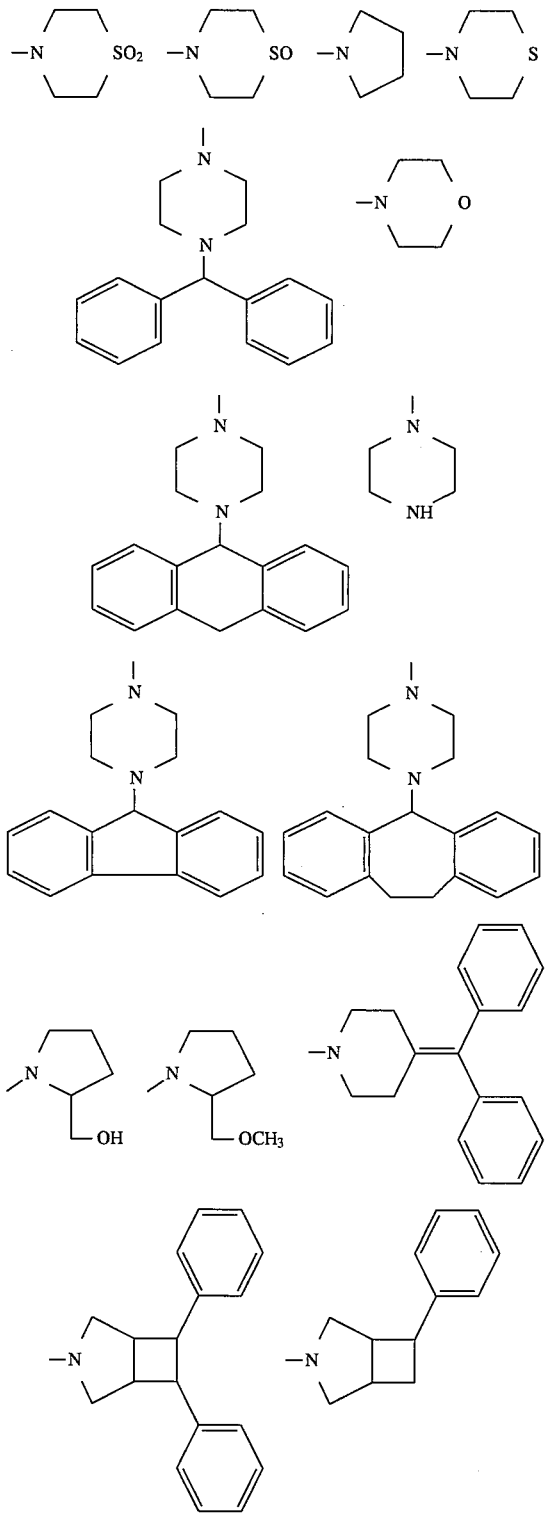

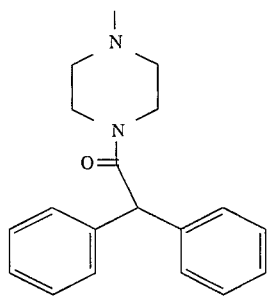

which may be unsubstituted or substituted with one or more substituents independently selected from the group consisting of $CF_3$, nitro, halogen, oxo, cyano, N,N-dimethylamino, CONHBzl, $CON(Bzl)_2$, $C_{1-6}$-alkyl (which may form a cyclic system), $C_{1-4}$-alkoxy, phenoxy, benzoxy, naphthyl, pyrimidyl, COOEt, COOBzl, $C_{3-6}$-cycloalkyl, pyrrolidinyl, piperidinyl, thienyl, pyrrolyl, $-CH_2-CO-NCH(CH_3)_2$, $-CH_2-CO-N(CH_2)_4$, $-CH_2-CO-N(CH_2)_4O$, benzyl (which may be substituted by up to three substituents independently selected from the group consisting of nitro, halogen, $CF_3$, thiomethyl or the corresponding sulfoxide or sulfone, thioethyl or the corresponding sulfoxide or sulfone, $C_{1-4}$-alkyl, and $C_{1-4}$-alkoxy), and phenyl (which may be substituted by up to three substituents independently selected from the group consisting of nitro, halogen, $CF_3$, thiomethyl, thioethyl, $C_{1-4}$-alkyl, and $C_{1-4}$-alkoxy).

5. Compounds of formula I according to claim 1 wherein b is zero.

6. Compounds of formula I according to claim 1 wherein d is zero, b is $-NR^4-CHG-CHK-CHL-CO-$, and Q is not a hydroxy or alkoxy group.

7. Compounds of formula I according to claim 1 wherein b and d are zero, and Q is not a hydroxy or alkoxy group.

8. Compounds of formula I according to claim 1 wherein d is 0 and $R^7$ is

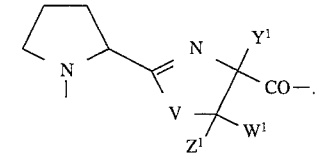

9. Compounds of formula I according to claim 1 wherein d is 0.

10. Compounds of formula I according to claim 1 wherein b and d are 1 and Q is a hydroxy, $C_{1-5}$-alkoxy or benzyloxy moiety.

11. A pharmaceutical composition comprising a pharmaceutically acceptable carrier and a therapeutically effective amount of a compound of claim 1.

12. A method of treating a tumor in a mammal comprising administering to a mammal bearing such a tumor, a tumor-inhibiting amount of a compound of claim 1.

13. The method of preparing compounds of formula I according to claim 1 characterized in that they are prepared according to known methods of peptide chemistry.

* * * * *

UNITED STATES PATENT AND TRADEMARK OFFICE
CERTIFICATE OF CORRECTION

PATENT NO.  : 5,502,032
DATED       : March 26, 1996
INVENTOR(S) : HAUPT et al.

It is certified that error appears in the above-indentified patent and that said Letters Patent is hereby corrected as shown below:

Column 66, claim 3, line 37, before "or phenyl" insert --or trifluoroethyl--.

Signed and Sealed this

Sixth Day of August, 1996

Attest:

BRUCE LEHMAN

Attesting Officer

Commissioner of Patents and Trademarks